(12) United States Patent
Zamierowski

(10) Patent No.: US 7,381,211 B2
(45) Date of Patent: Jun. 3, 2008

(54) MEDICAL CLOSURE SCREEN DEVICE AND METHOD

(75) Inventor: David S. Zamierowski, Shawnee Mission, KS (US)

(73) Assignee: KCI Licensing, Inc., San Antonio, TX (US)

(*) Notice: Subject to any disclaimer, the term of this patent is extended or adjusted under 35 U.S.C. 154(b) by 772 days.

(21) Appl. No.: 10/224,852

(22) Filed: Aug. 21, 2002

(65) Prior Publication Data

US 2004/0039415 A1    Feb. 26, 2004

(51) Int. Cl.
*A61B 17/08* (2006.01)
*A61D 1/00* (2006.01)

(52) U.S. Cl. ....................................... 606/216
(58) Field of Classification Search ............... 606/216, 606/221, 217
See application file for complete search history.

(56) References Cited

U.S. PATENT DOCUMENTS

| | | |
|---|---|---|
| 221,427 A | 11/1879 | Sherman |
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,066,672 A | 12/1962 | Crosby, Jr. |
| 3,115,138 A | 12/1963 | McElvenny et al. |
| 3,367,332 A | 2/1968 | Groves |
| 3,520,300 A | 7/1970 | Flower |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |

(Continued)

FOREIGN PATENT DOCUMENTS

AU    550575 A1    8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, . . . .

(Continued)

*Primary Examiner*—Michael J. Hayes
*Assistant Examiner*—Christina Gettman

(57) ABSTRACT

A medical closure screen device for a separation of first and second tissue portions is provided, which includes a mesh screen comprising tubular vertical risers, vertical strands with barbed filaments, and horizontal spacers connecting the risers and strands in a grid-like configuration. An optional perimeter member partly surrounds the screen and can comprise a perimeter tube fluidically coupled with the vertical risers to form a tubing assembly. Various input/output devices can optionally be connected to the perimeter tube ends for irrigating and/or draining the separation according to methodologies of the present invention. Separation closure, irrigation and drainage methodologies are disclosed utilizing various combinations of closure screens, tubing, sutures, fluid transfer elements and gradient force sources. The use of mechanical forces associated with barbed strands for repositionably securing separated tissues together is disclosed. The use of same for eliminating or reducing the formation of subcutaneous voids or pockets, which can potentially form hematoma and seroma effects, is also disclosed.

66 Claims, 31 Drawing Sheets

U.S. PATENT DOCUMENTS

| | | | |
|---|---|---|---|
| 4,139,004 A | 2/1979 | Gonzalez | |
| 4,165,748 A | 8/1979 | Johnson | |
| 4,233,969 A | 11/1980 | Lock et al. | |
| 4,245,630 A | 1/1981 | Lloyd et al. | |
| 4,248,232 A | 2/1981 | Engelbrecht et al. | |
| 4,259,959 A * | 4/1981 | Walker | 606/221 |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman et al. | |
| 4,392,853 A | 7/1983 | Muto | |
| 4,392,858 A | 7/1983 | George et al. | |
| 4,419,093 A | 12/1983 | Deaton | |
| 4,419,097 A | 12/1983 | Rowland | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vailancourt | |
| 4,540,412 A | 9/1985 | Van Overloop | |
| 4,543,100 A | 9/1985 | Brodsky | |
| 4,548,202 A * | 10/1985 | Duncan | 606/220 |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,696,301 A * | 9/1987 | Barabe | 606/216 |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,449 A | 5/1989 | Richmond et al. | |
| 4,828,546 A | 5/1989 | McNeil et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,976,726 A | 12/1990 | Haverstock | |
| 4,985,019 A | 1/1991 | Michelson | |
| 5,007,921 A | 4/1991 | Brown | |
| 5,007,936 A | 4/1991 | Woolson | |
| 5,019,083 A | 5/1991 | Klapper et al. | |
| 5,037,397 A | 8/1991 | Kalt et al. | |
| 5,045,054 A | 9/1991 | Hood et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,112,338 A | 5/1992 | Anspach, III | |
| 5,134,994 A | 8/1992 | Say | |
| 5,149,331 A | 9/1992 | Ferdman et al. | |
| 5,167,613 A | 12/1992 | Karami et al. | |
| 5,169,399 A | 12/1992 | Ryland et al. | |
| 5,176,663 A | 1/1993 | Svedman et al. | |
| 5,215,522 A | 6/1993 | Page et al. | |
| D337,639 S | 7/1993 | Beckman | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,291,887 A | 3/1994 | Stanley et al. | |
| 5,298,015 A | 3/1994 | Komatsuzaki et al. | |
| 5,318,570 A | 6/1994 | Hood et al. | |
| 5,342,376 A | 8/1994 | Ruff | |
| 5,344,415 A | 9/1994 | Debusk et al. | |
| 5,358,494 A | 10/1994 | Svedman | |
| 5,383,897 A * | 1/1995 | Wholey | 606/213 |
| 5,423,885 A * | 6/1995 | Williams | 623/1.17 |
| 5,437,622 A | 8/1995 | Carion | |
| 5,437,651 A | 8/1995 | Todd et al. | |
| 5,507,833 A | 4/1996 | Bohn | |
| 5,522,901 A | 6/1996 | Thomas et al. | |
| 5,527,293 A | 6/1996 | Zamierowski | |
| D372,309 S | 7/1996 | Heldreth | |
| 5,549,584 A | 8/1996 | Gross | |
| 5,556,375 A | 9/1996 | Ewall | |
| 5,580,353 A | 12/1996 | Mendes | |
| 5,584,859 A * | 12/1996 | Brotz | 606/228 |
| 5,607,388 A | 3/1997 | Ewall | |
| 5,630,819 A | 5/1997 | Ashby et al. | |
| 5,636,643 A | 6/1997 | Argenta et al. | |
| 5,645,081 A | 7/1997 | Argenta et al. | |
| 5,716,360 A | 2/1998 | Baldwin et al. | |
| 5,738,686 A | 4/1998 | Budein-Meesenburg | |
| 5,785,700 A | 7/1998 | Olson | |
| 5,800,546 A | 9/1998 | Marik et al. | |
| 5,827,246 A | 10/1998 | Bowen | |
| 5,846,244 A | 12/1998 | Cripe | |
| 5,911,222 A | 6/1999 | Lawrence et al. | |
| 5,921,972 A | 7/1999 | Skow | |
| 5,931,855 A * | 8/1999 | Buncke | 606/228 |
| 5,941,859 A | 8/1999 | Lerman | |
| 6,071,267 A | 6/2000 | Zamierowski | |
| 6,113,618 A | 9/2000 | Nic | |
| 6,126,659 A | 10/2000 | Wack | |
| 6,135,116 A | 10/2000 | Vogel et al. | |
| 6,142,982 A | 11/2000 | Hunt et al. | |
| 6,146,423 A | 11/2000 | Cohen et al. | |
| 6,159,246 A | 12/2000 | Mendes et al. | |
| 6,174,306 B1 | 1/2001 | Fleischmann | |
| 6,179,804 B1 | 1/2001 | Satterfield | |
| 6,190,391 B1 | 2/2001 | Stubbs | |
| 6,190,392 B1 | 2/2001 | Vandewalle | |
| 6,241,747 B1 * | 6/2001 | Ruff | 606/216 |
| 6,270,517 B1 | 8/2001 | Brotz | |
| RE37,358 E | 9/2001 | Del Rio et al. | |
| 6,287,316 B1 | 9/2001 | Agarwal et al. | |
| 6,293,929 B1 | 9/2001 | Smith et al. | |
| 6,345,623 B1 | 2/2002 | Heaton et al. | |
| 6,355,215 B1 | 3/2002 | Poggie et al. | |
| 6,377,653 B1 | 4/2002 | Lee et al. | |
| 6,398,767 B1 | 6/2002 | Fleischmann | |
| 6,430,427 B1 | 8/2002 | Lee et al. | |
| 6,488,643 B1 | 12/2002 | Tumey et al. | |
| 6,493,568 B1 | 12/2002 | Bell et al. | |
| 6,500,209 B1 | 12/2002 | Kolb | |
| 6,503,281 B1 | 1/2003 | Mallory | |
| 6,553,998 B2 | 4/2003 | Heaton et al. | |
| 6,620,132 B1 | 9/2003 | Skow | |
| 6,626,891 B2 | 9/2003 | Ohmstede | |
| 6,645,226 B1 * | 11/2003 | Jacobs et al. | 606/215 |
| 6,669,735 B1 | 12/2003 | Pelissier | |
| 6,685,681 B2 | 2/2004 | Lockwood et al. | |
| 6,695,823 B1 | 2/2004 | Lina et al. | |
| 6,726,706 B2 * | 4/2004 | Dominguez | 606/228 |
| 6,752,794 B2 | 6/2004 | Lockwood et al. | |
| 6,800,074 B2 | 10/2004 | Henley et al. | |
| 6,814,079 B2 | 11/2004 | Heaton et al. | |
| 6,991,643 B2 * | 1/2006 | Saadat | 606/221 |
| 2002/0022861 A1 | 2/2002 | Jacobs et al. | |
| 2002/0029063 A1 | 3/2002 | Wittman | |
| 2002/0077661 A1 | 6/2002 | Saadat | |

| | | | |
|---|---|---|---|
| 2002/0099447 | A1 | 7/2002 | Mears et al. |
| 2002/0115951 | A1 | 8/2002 | Norstream et al. |
| 2002/0116067 | A1 | 8/2002 | Mears et al. |
| 2002/0120185 | A1 | 8/2002 | Johnson |
| 2002/0143286 | A1 | 10/2002 | Tumey |
| 2002/0183565 | A1 | 12/2002 | Leavanoni et al. |
| 2003/0050594 | A1 | 3/2003 | Zamierowski |
| 2003/0097135 | A1 | 5/2003 | Penenberg |
| 2004/0039415 | A1 | 2/2004 | Zamierowski |
| 2005/0043818 | A1 | 2/2005 | Bellon et al. |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2220357 | 1/1990 |
| GB | 2235877 | 3/1991 |
| GB | 2333965 A | 8/1999 |
| GB | 2329127 B | 8/2000 |
| SG | 71559 | 4/2002 |
| WO | WO 80/02182 | 10/1980 |
| WO | WO 93/09727 | 5/1993 |
| WO | WO/94/20041 | 9/1994 |
| WO | WO 96/05873 | 2/1996 |
| WO | WO 97/18007 | 5/1997 |
| WO | WO 99/13793 | 9/1998 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457; . . . .

John Masters; Letter to the editor: British Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53 . . . .

George V. Letsou, M.D., et al: Stimulation of Adenylate Cyclase Activity in Cultured Endothelial Cells Subjected to Cyclic Stretch; Journal of Cardiovascular Surgery, 31, 1990.

PCT International Search Report; PCT international Application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treament in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means of Vacuum Therapy; Vestnik Khirurgi.

International Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

Miyauchi, Takayuki et al., "Repair of Incisional Hernia with Prolene Hernia System", *The Journal of Medical Investigation*, vol. 50, pp. 108-111, 2003: received for publication Aug. 8, 2002.

\* cited by examiner

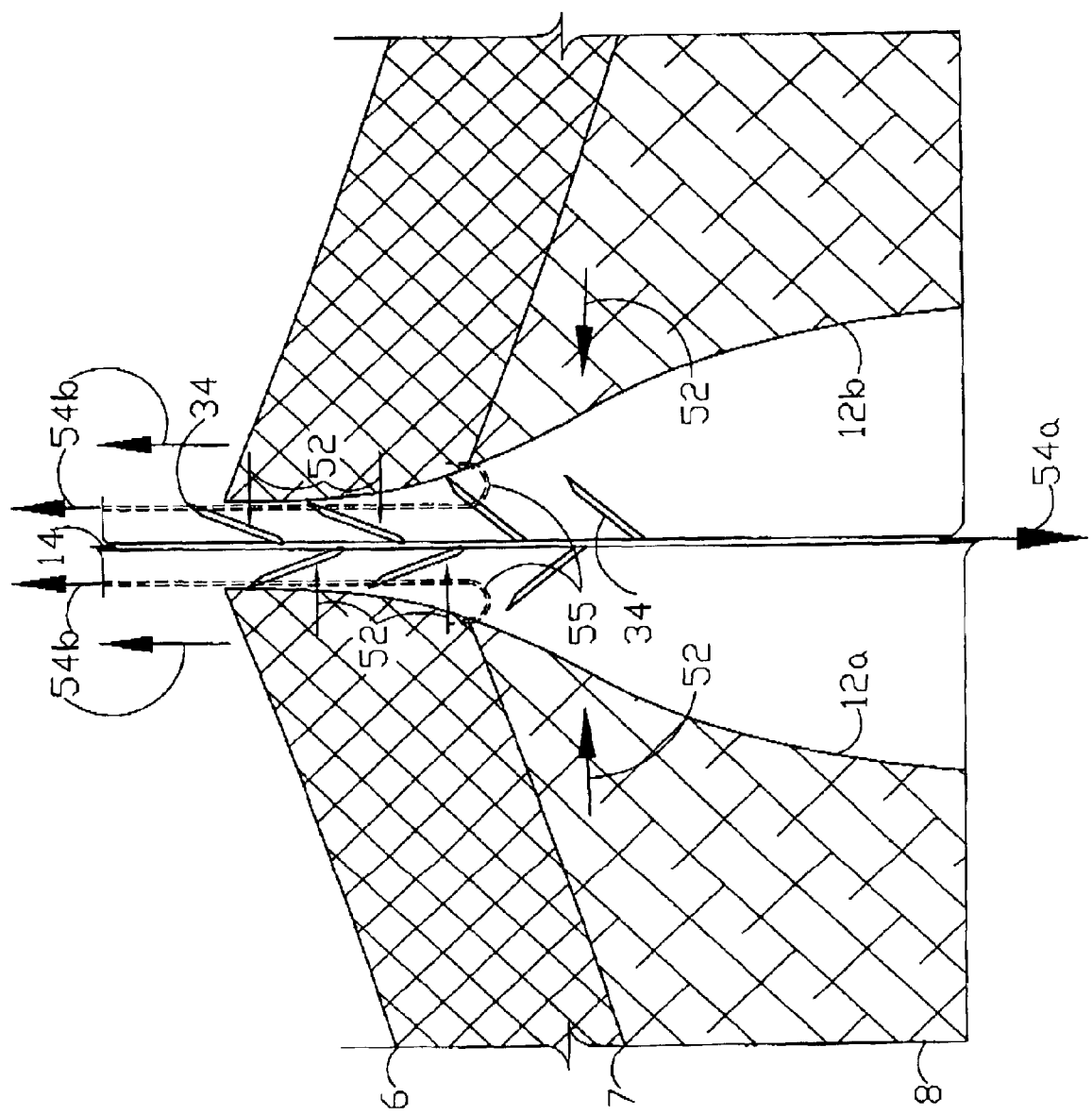

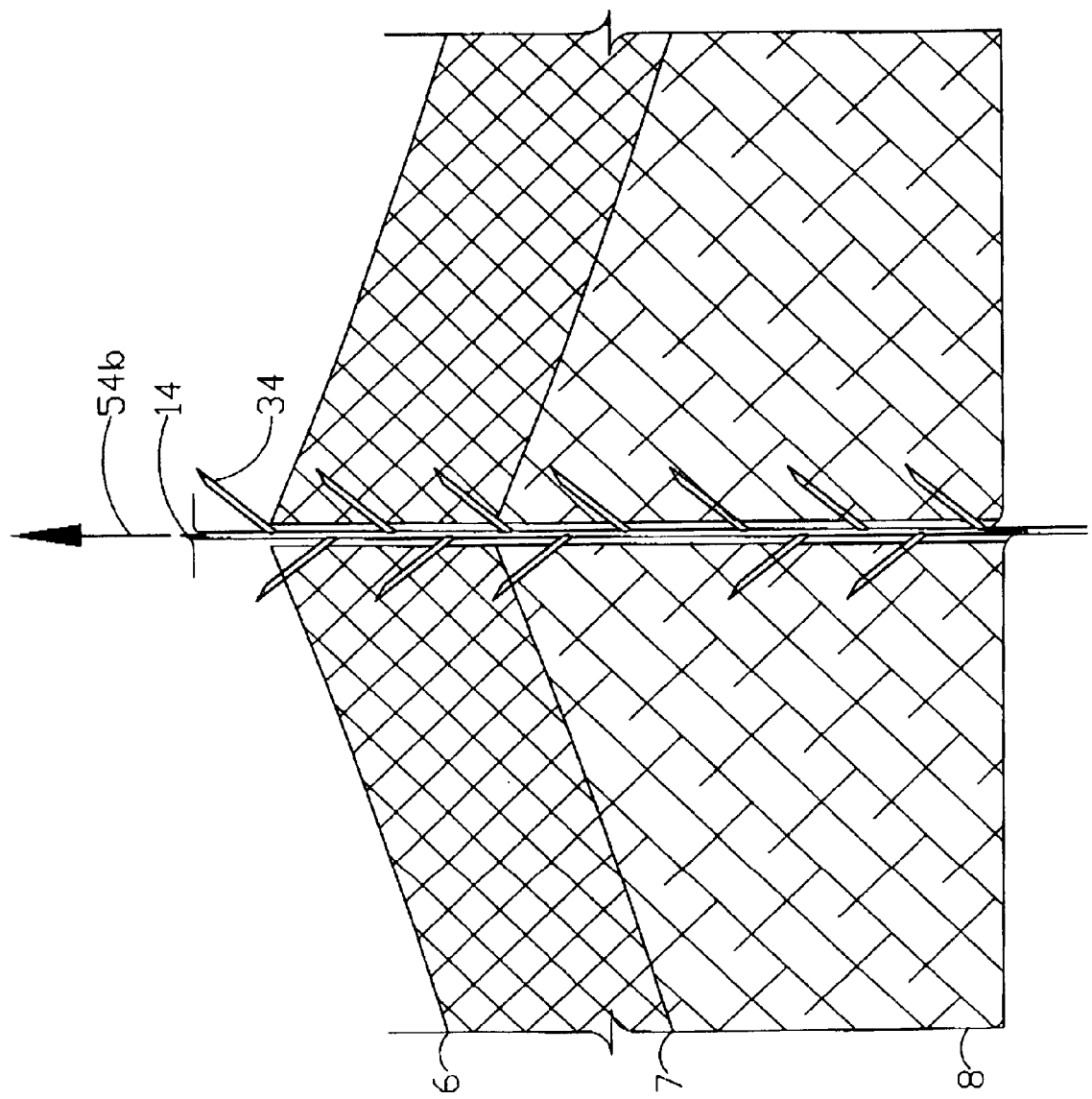

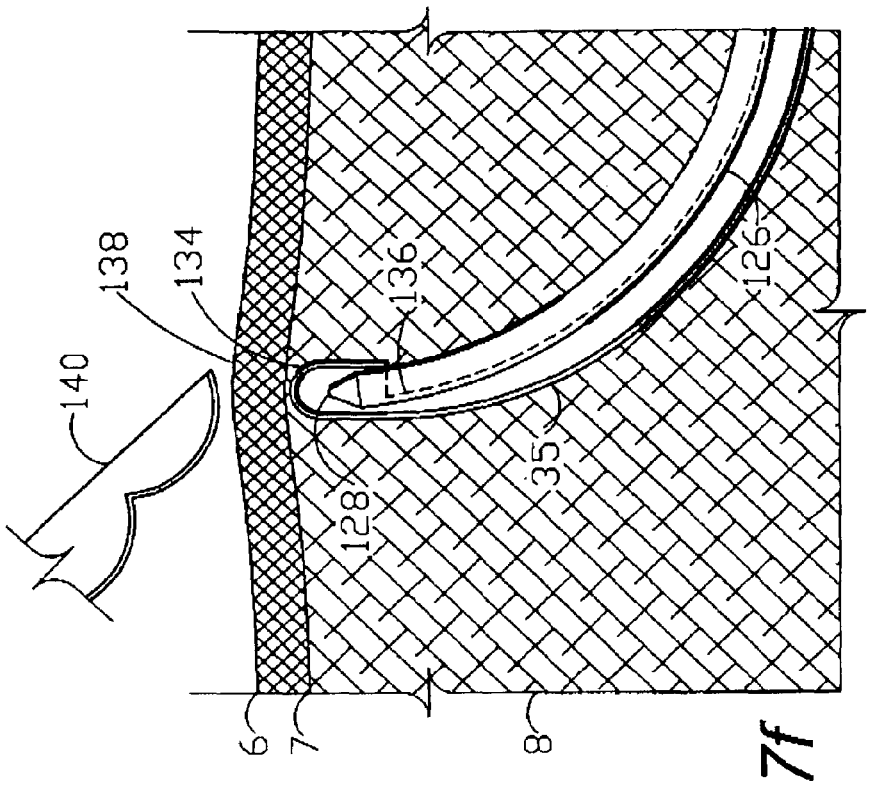
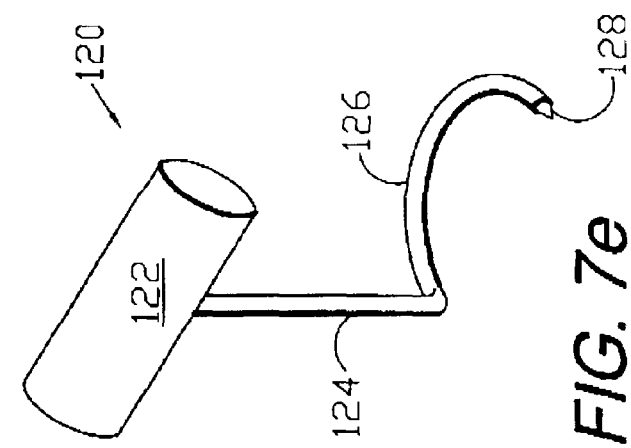
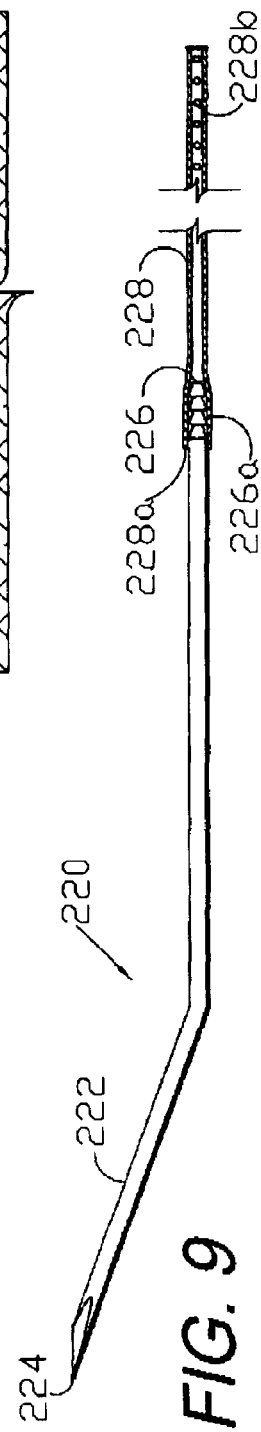

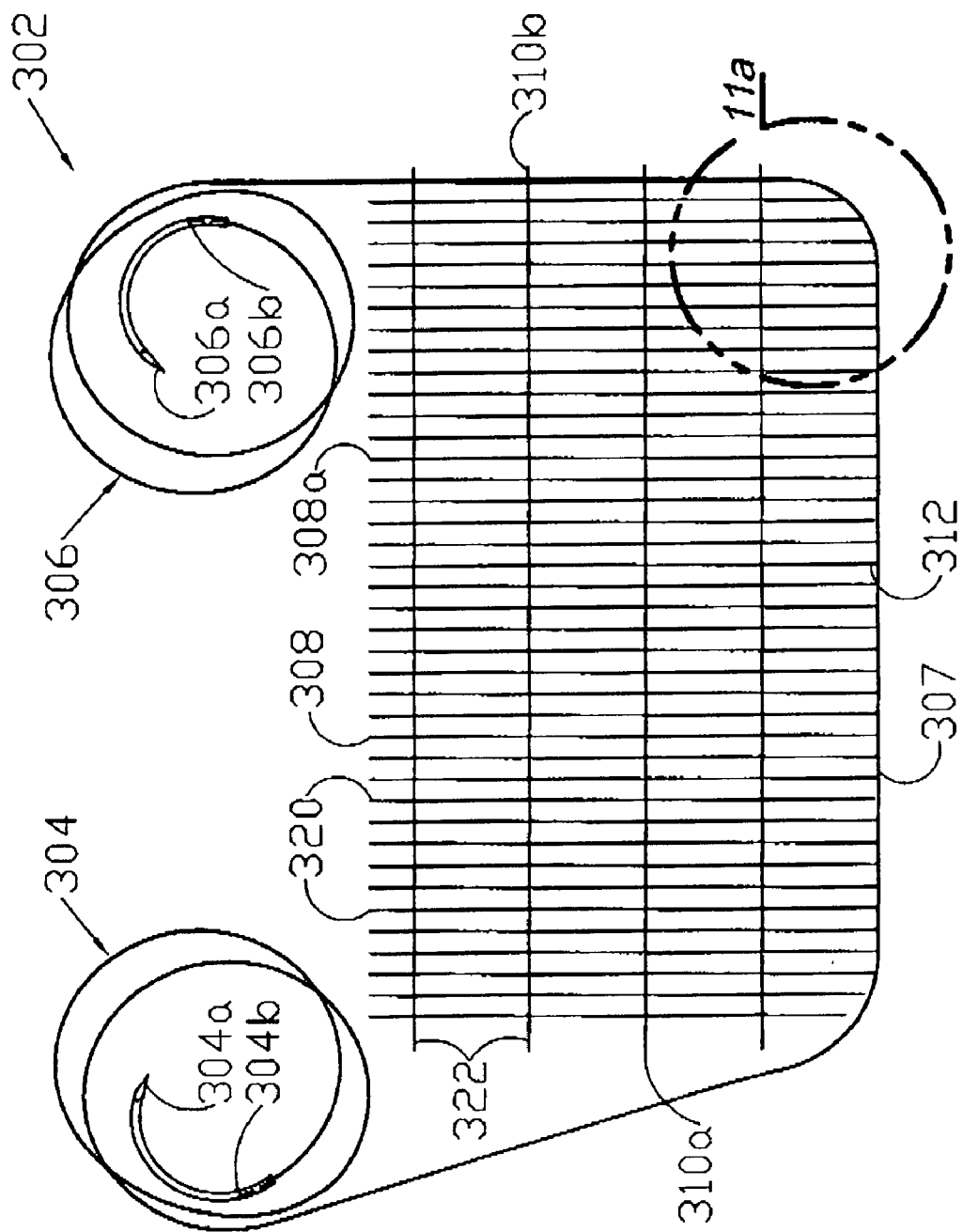

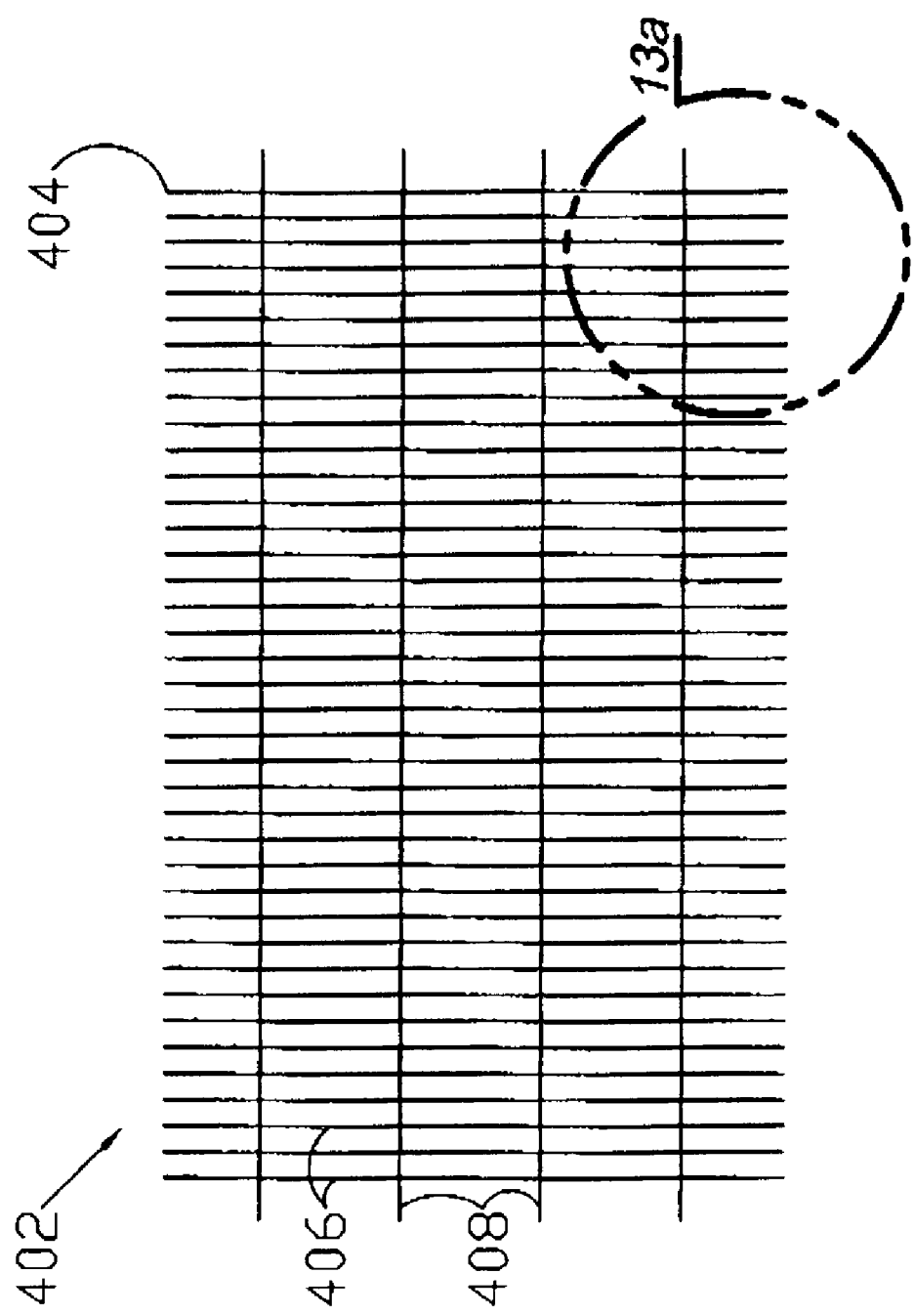

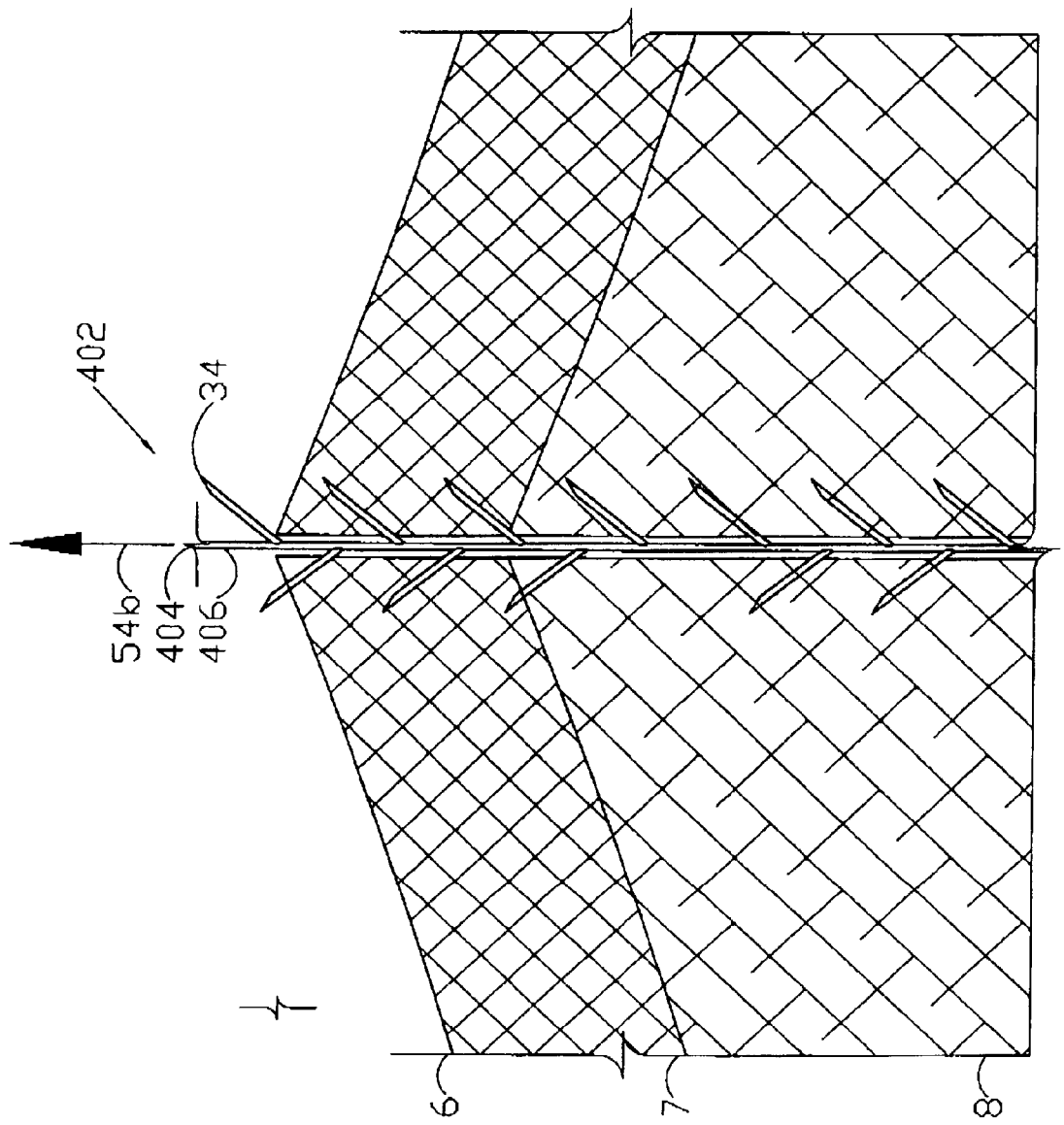

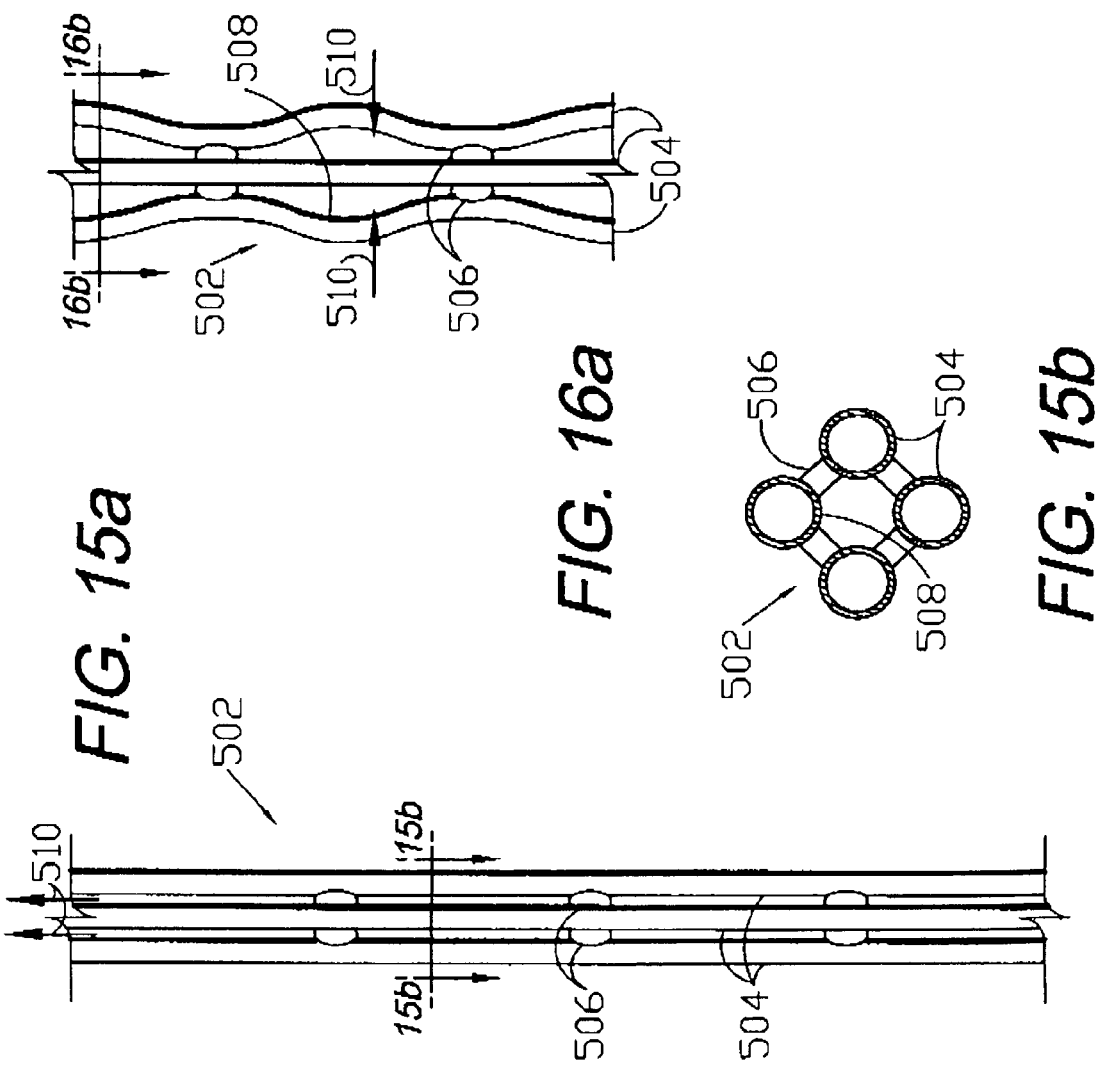

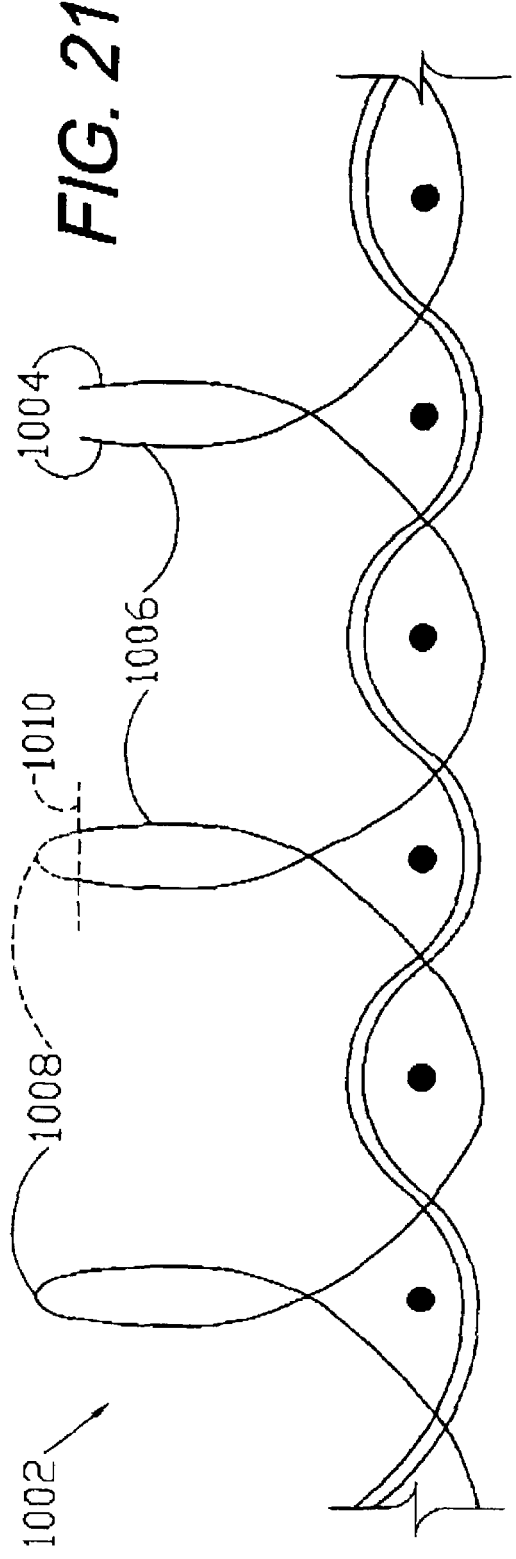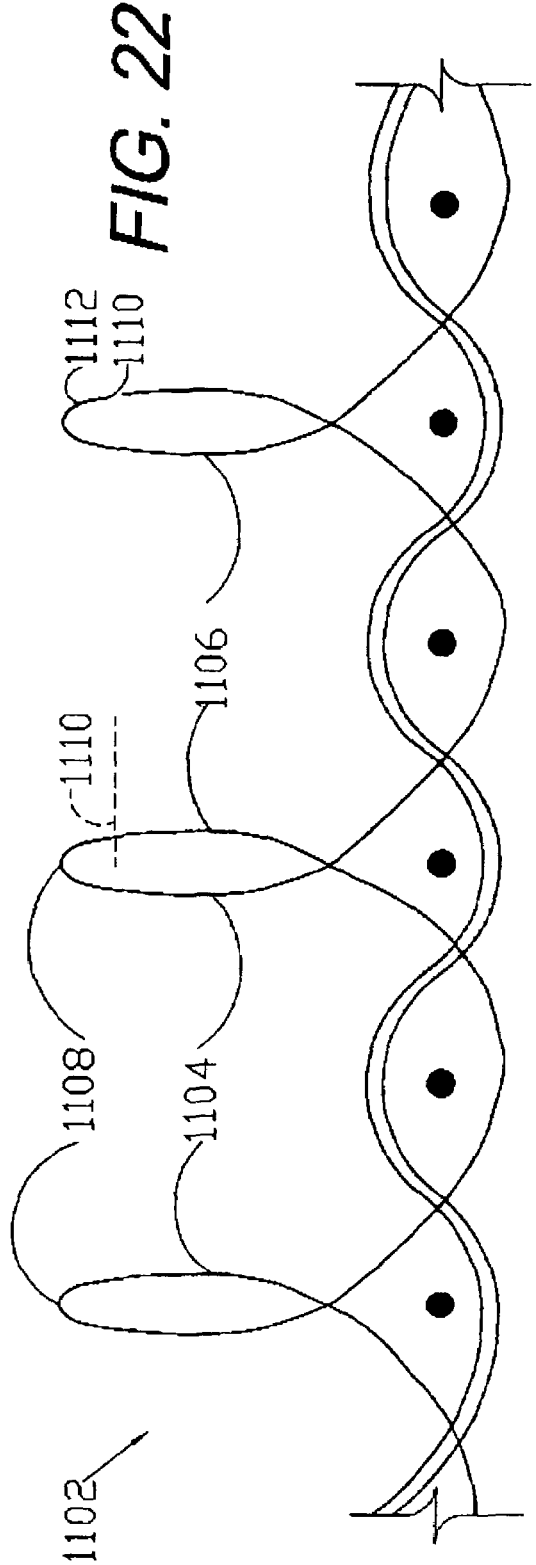

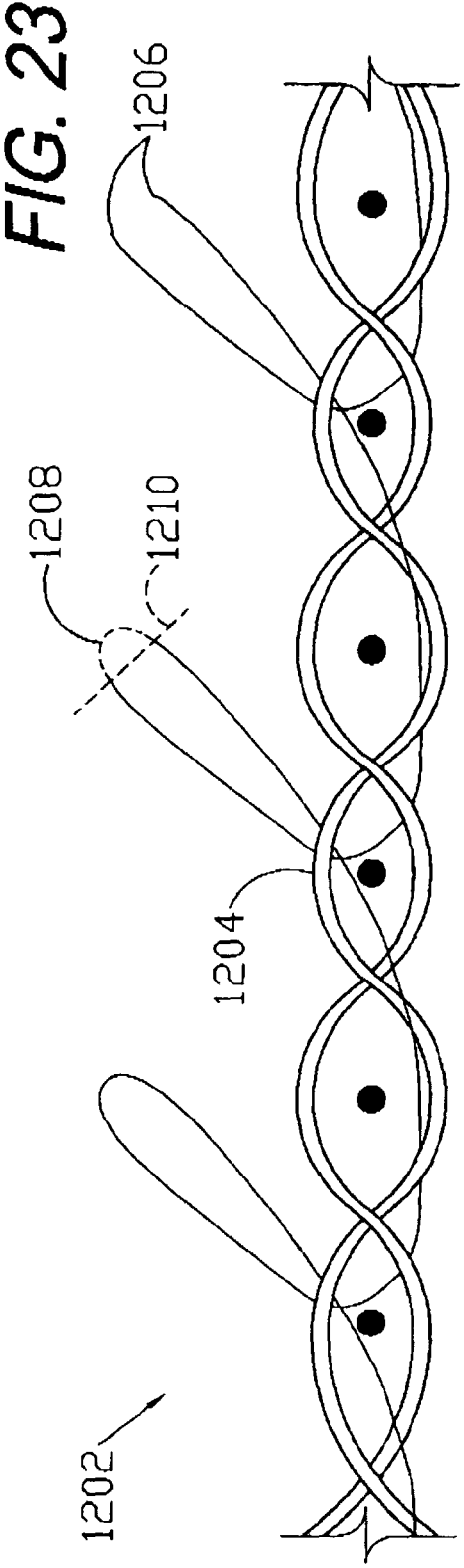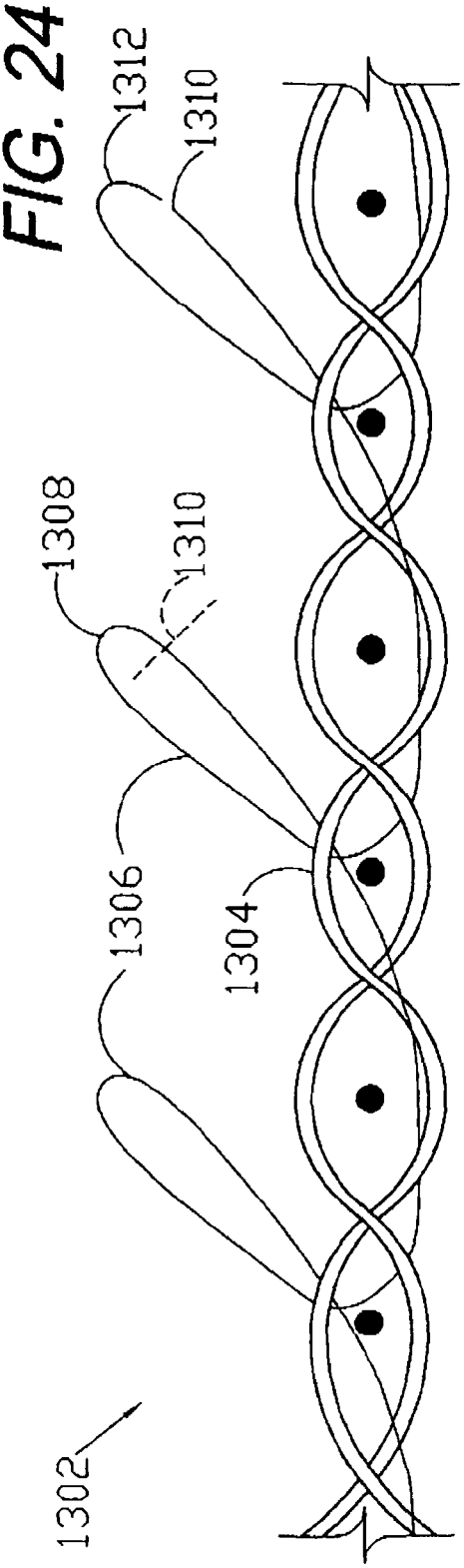

MEDICAL CLOSURE SCREEN DEVICE AND METHOD

FIELD OF THE INVENTION

The present invention relates generally to medical closure and wound fluid management devices, and in particular to an absorbable screen closure member for closing tissue separations, such as incisions and wounds.

DESCRIPTION OF THE PRIOR ART

In the medical field, cutaneous incisions are commonly performed in surgery to provide access to underlying tissue, organs, joints, skeletal structure, etc. Incision and closure techniques are an important part of surgery in general. They tend to occupy surgical teams and other resources for significant portions of many surgical procedures.

Surgeons generally strive to minimize the traumatic and scarring effects of surgery on their patients by both minimizing the incisions, and by employing a variety of closure techniques which tend to reduce postoperative swelling, bleeding, seroma, infection and other undesirable postoperative side effects. For example, the fields of endoscopic-assisted surgery, microscopic surgery, and computer-enhanced instrumentation (e.g., the DaVinci System available from Intuitive Surgical, Inc. of Sunnyvale, Calif.) are generally concerned with minimally invasive surgery ("MIS") procedures and techniques, which have proven to be increasingly popular. Such popularity is at least partly due not only to the minimally-sized scars left by such techniques, but also to the minimal trauma to the fascia and muscle layers and the correspondingly faster recoveries this allows. However, surgeons must balance such considerations with providing adequate access to perform various surgical procedures.

Some surgical procedures, by their nature, must include long incisions. Examples include cutaneous excisional procedures such as "lifts" and reduction procedures, flap procedures for closure of defects, and many bariatric procedures.

The "first intention" (primary intention healing) in surgery is to "close" the incision. For load-bearing tissues, such as bone, fascia, and muscle, this requires substantial material, be it suture material, staples, or plates and screws. For the wound to be "closed," the epithelial layer must seal. To accomplish this, the "load bearing" areas of the cutaneous and subcutaneous layers (i.e., the deep dermal elastic layer and the superficial fascia or fibrous layers of the adipose tissue, respectively) must also at least be held in approximation. Important considerations include controlling infection and bleeding, reducing scarring, eliminating the potential of hematoma, seroma, and "dead-space" formation and managing pain. Dead space problems are more apt to occur in the subcutaneous closure. Relatively shallow incisions can normally be closed with surface-applied closure techniques, such as sutures, staples, glues, and adhesive tape strips. However, deeper incisions may well require not only skin surface closure, but also time-consuming placement of multiple layers of sutures in the load-bearing planes. Absorbable sutures are commonly used for this purpose and comprise an important class of surgical sutures. Depending on various factors, absorbable sutures typically dissolve over a period of a few days to a few months. Commercially available examples include Monocryl® monofilament absorbable synthetic sutures comprising a poliglecaprone and PDS® (polydrioxanone) and Vicryl® (polyglactin) sutures, all available from Ethicon, Inc., of Somerville, N.J.

Surgical mesh represents another important class of surgical closure devices. Applications include reconstruction, hernia repair, and organ repair. In such procedures, surgical mesh fabric prostheses are inserted into patients through either open surgery or endoscopic (MIS) procedures. Knitted surgical mesh for hernia repair is disclosed in the Agarwal et al. U.S. Pat. No. 6,287,316, which is assigned to Ethicon, Inc. Another Ethicon, Inc. patent, Duncan U.S. Pat. No. 4,548,202, discloses mesh tissue fasteners including various fastening members with spaced-apart legs for passing through tissue portions. Another closure procedure involves the placement of pins or rods through skin edge or bone followed by the placement of an external clamp or fixator device spanning the wound and frequently incorporating a worm-screw apparatus capable of progressive tightening over time to effect closure, stabilization or distraction.

Fluid management represents another important aspect of both open and minimally invasive surgery. Postoperative fluid drainage can be accomplished with various combinations of tubes, sponges, and porous materials adapted for gathering and draining bodily fluids. The prior art includes technologies and methodologies for assisting drainage. For example, the Zamierowski U.S. Pat. Nos. 4,969,880; 5,100,396; 5,261,893; 5,527,293; and 6,071,267 disclose the use of pressure gradients, i.e., vacuum and positive pressure, to assist with fluid drainage from wounds, including surgical incision sites. Such pressure gradients can be established by applying porous sponge material either internally or externally to a wound, covering same with a permeable, semi-permeable, or impervious membrane, and connecting a suction vacuum source thereto. Fluid drawn from the patient is collected for disposal. Such fluid control methodologies have been shown to achieve significant improvements in patient healing. Another aspect of fluid management, post-operative and otherwise, relates to the application of fluids to wound sites for purposes of irrigation, infection control, pain control, growth factor application, etc. Wound drainage devices are also used to achieve fixation and immobility of the tissues, thus aiding healing and closure. This can be accomplished by both internal closed wound drainage and external vacuum devices. Fixation of tissues in apposition can also be achieved by bolus tie-over dressings (Stent dressings), taping, strapping and (contact) casting.

Heretofore, there has not been available a medical closure screen with the advantages and features of the present invention, including the combination of same with vacuum-assisted closure.

SUMMARY OF THE INVENTION

In the practice of the present invention, a medical closure screen device is provided, which includes a mesh screen comprising tubular vertical risers, barbed filaments therebetween and horizontal spacers. An optional perimeter member partly surrounds the screen member and can comprise a perimeter tube fluidically coupled with the vertical risers to form a tubing assembly. The tubing assembly cooperates with the vertical risers to extract fluid from the tissue separation in a drain mode and to introduce fluid thereinto in an irrigate mode. In one embodiment of the invention the tubing assembly is fluidically coupled to a vacuum source to facilitate drainage. In another embodiment of the invention, the perimeter tube is passed through the surrounding tissue to secure the screen member in place. Fluid transfer elements, such as sponges, are optionally placed adjacent to and over an extension of the screen for fluid transfer, for example, in conjunction with a vacuum or pump source.

Another embodiment of the invention includes a suture connected to the screen and adapted for securing same in a tissue separation. Alternative embodiment vertical risers are also disclosed, and can provide active fluid transfer utilizing the patient's body dynamics. Yet another alternative embodiment of the present invention utilizes the screen barbs for mechanical fixation in a separation for closure of same. Separation closure, irrigation and drainage methodologies are disclosed utilizing various combinations of closure screens, tubing, sutures, fluid transfer elements and gradient force sources. The closure screen of the present invention uses mechanical and other forces associated with screens and barbed strands for securing separated tissues together and for eliminating or reducing the formation of subcutaneous voids or pockets, which can potentially form hematoma and seroma effects.

BRIEF DESCRIPTION OF THE DRAWINGS

FIG. 6a is an enlarged, fragmentary, cross-sectional view of the closure screen in a tissue separation, with skin hooks shown in hidden lines for positioning the separated tissue portions along the closure screen.

FIG. 6b is an enlarged, fragmentary, cross-sectional view of the closure screen in a substantially closed tissue separation.

FIGS. 7a-f show a tissue separation closure procedure embodying the method of the present invention and utilizing optional sponge or foam fluid transfer elements and a tubing placement tool.

FIG. 9 shows a needle mounting a length of drain tubing and adapted for passing same through tissue.

FIG. 10 is a side elevational view of a closure screen comprising an alternative embodiment of the present invention, with a perimeter suture.

FIG. 12 is a side elevational view of a screen-only closure screen comprising an alternative embodiment of the present invention.

FIGS. 14a-g show a tissue separation closure procedure utilizing the screen-only embodiment of the closure screen.

FIG. 15a is a side elevational view of a modified vertical riser with flexible, multi-tube risers forming a fluid passage.

FIG. 15b is a cross-sectional view thereof, taken generally along line 15b-15b in FIG. 15a.

FIG. 16a is a fragmentary, side elevational view thereof, shown in a compressed configuration.

FIG. 16b is a cross-sectional view thereof, taken generally along line 16b-16b in FIG. 16a.

FIG. 17 is a cross-sectional view of another modified vertical riser construction with risers bundled in a different configuration, with barbs.

FIG. 21 is an enlarged, cross-sectional view of a closure screen comprising an alternative embodiment of the present invention, with barbs formed by cutting off the ends of looped filaments.

FIG. 22 is an enlarged, cross-sectional view of a closure screen comprising an alternative embodiment of the present invention, with barbs forming hooks and constructed by cutting looped filaments.

FIG. 23 is an enlarged, cross-sectional view of a closure screen comprising yet another alternative embodiment of the present invention, with barbs formed by cutting off the ends of looped filaments, which are laid over in a common direction or orientation.

FIG. 24 is an enlarged, cross-sectional view of a closure screen comprising a further alternative embodiment of the present invention, with barbs forming hooks and constructed by cutting looped filaments, which are laid over in a common direction or orientation.

DETAILED DESCRIPTION OF THE PREFERRED EMBODIMENTS

I. Introduction and Environment

Figure 1:
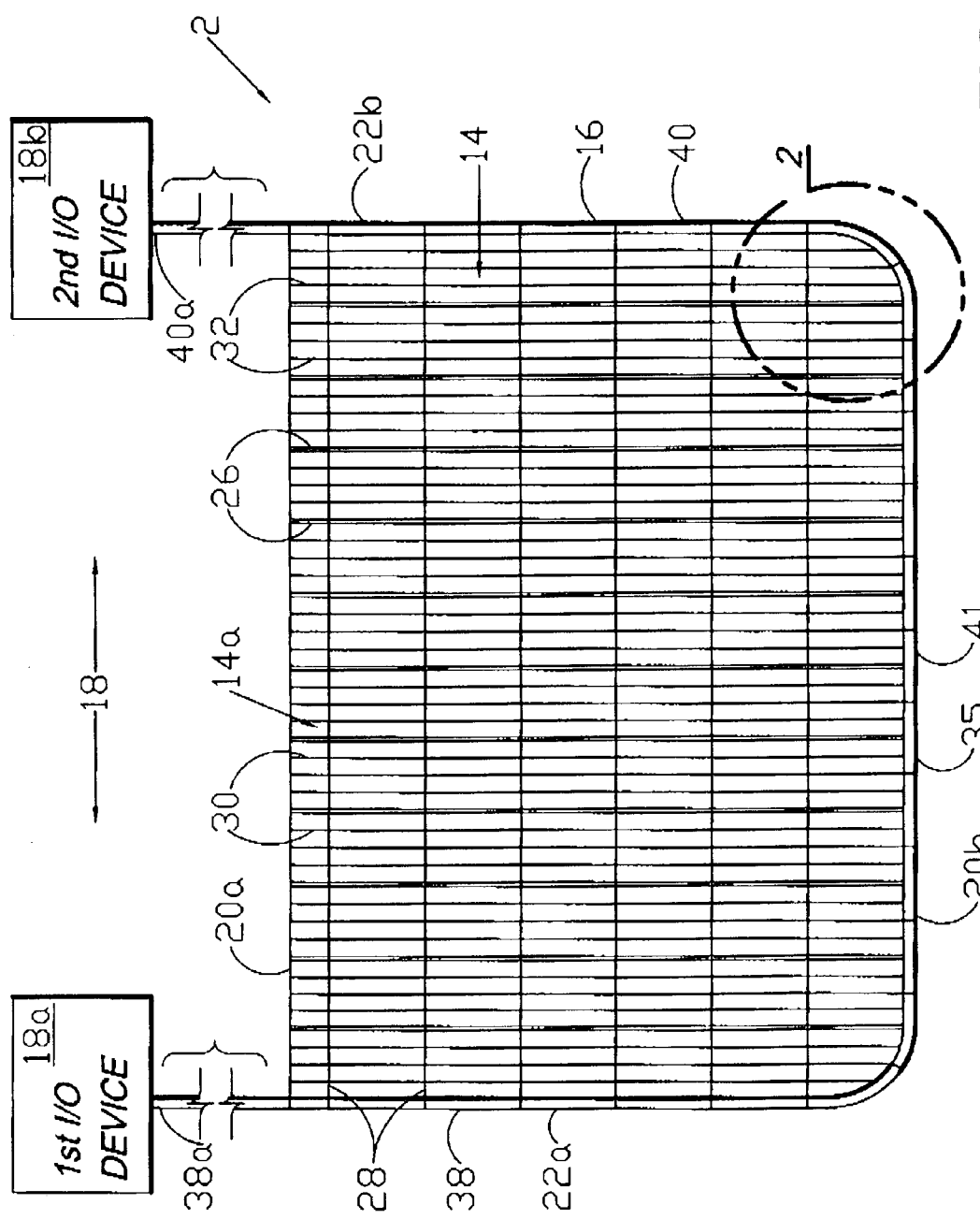
FIG. 1 is a side elevational view of a medical closure screen device embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. The words "horizontal" and "vertical" generally mean side-to-side and end-to-end, respectively. Said terminology will include the words specifically mentioned, derivatives thereof and words of a similar import.

Figure 5A:
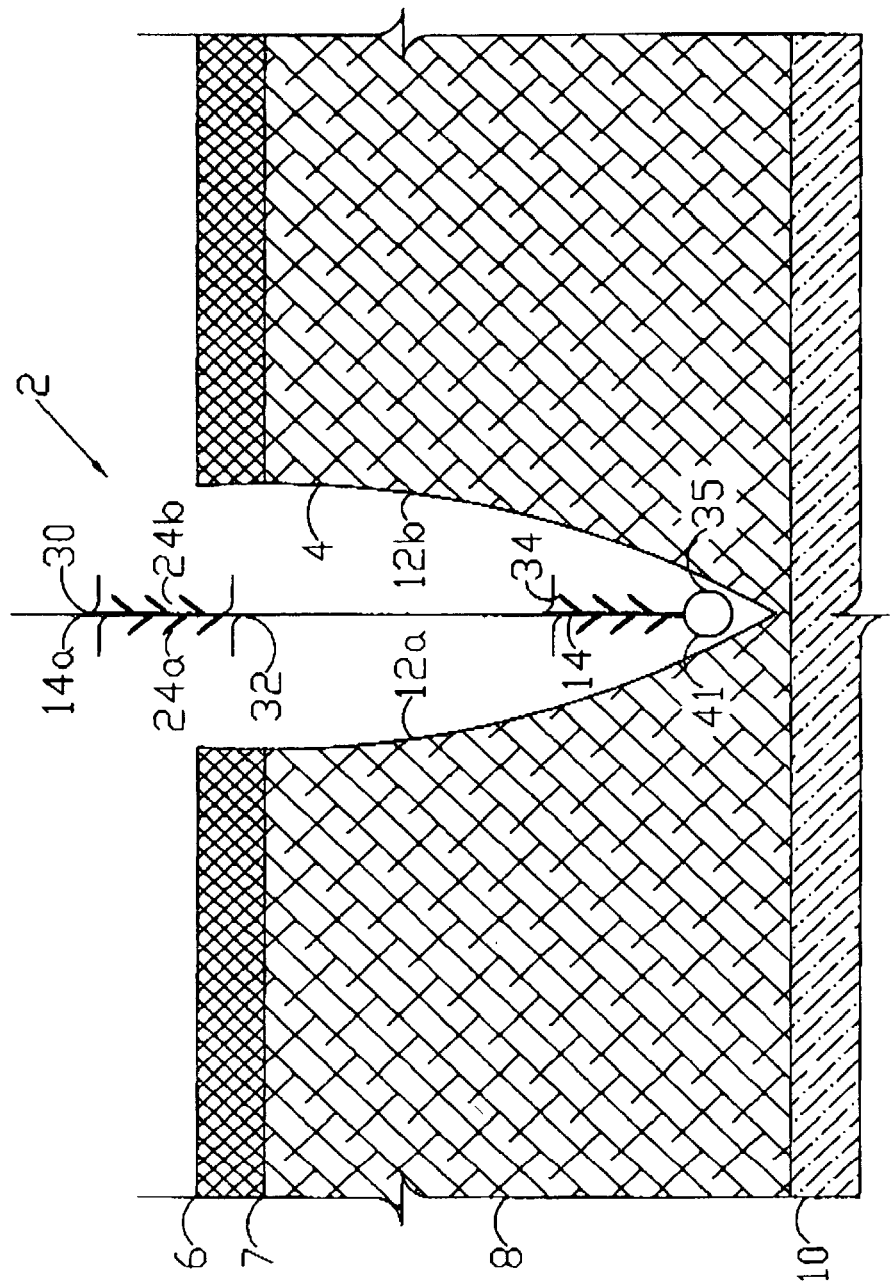
FIGS. 5a-e show a tissue separation closure procedure embodying the method of the present invention.

Referring to the drawings in more detail, the reference numeral 2 generally designates a medical closure screen device or system embodying the present invention. Without limitation on the generality of useful applications of the closure screen system 2, the primary application disclosed herein is for assistance with the closing, draining, irrigating and healing of a separation of first and second tissue portions, such as a wound or incision 4. As shown in FIG. 5a, the wound 4 extends from and is open at the dermis 6, through the deep dermal layer 7 and the subcutaneous layer 8, and to approximately the fascia 10. The wound 4 displays edges 12a,b, which correspond to first and second tissue portions. The closure screen device 2 generally comprises a screen 14, a screen perimeter member 16 and an input/output (I/O) subsystem 18.

II. Screen 14

Figure 3:
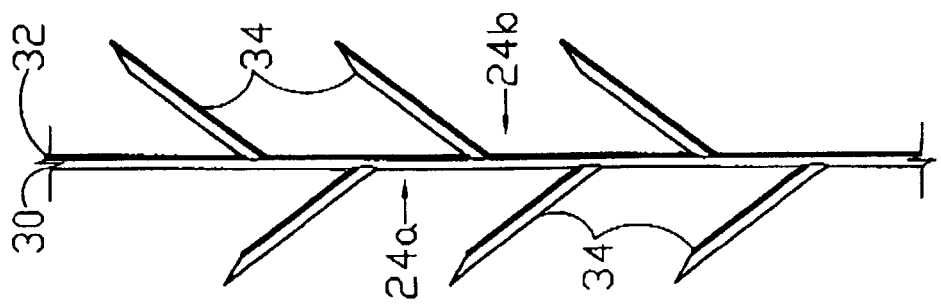
FIG. 3 is an enlarged, fragmentary, side elevational view thereof, taken generally along line 3-3 in FIG. 2, and particularly showing a barbed strand.
Figure 2:
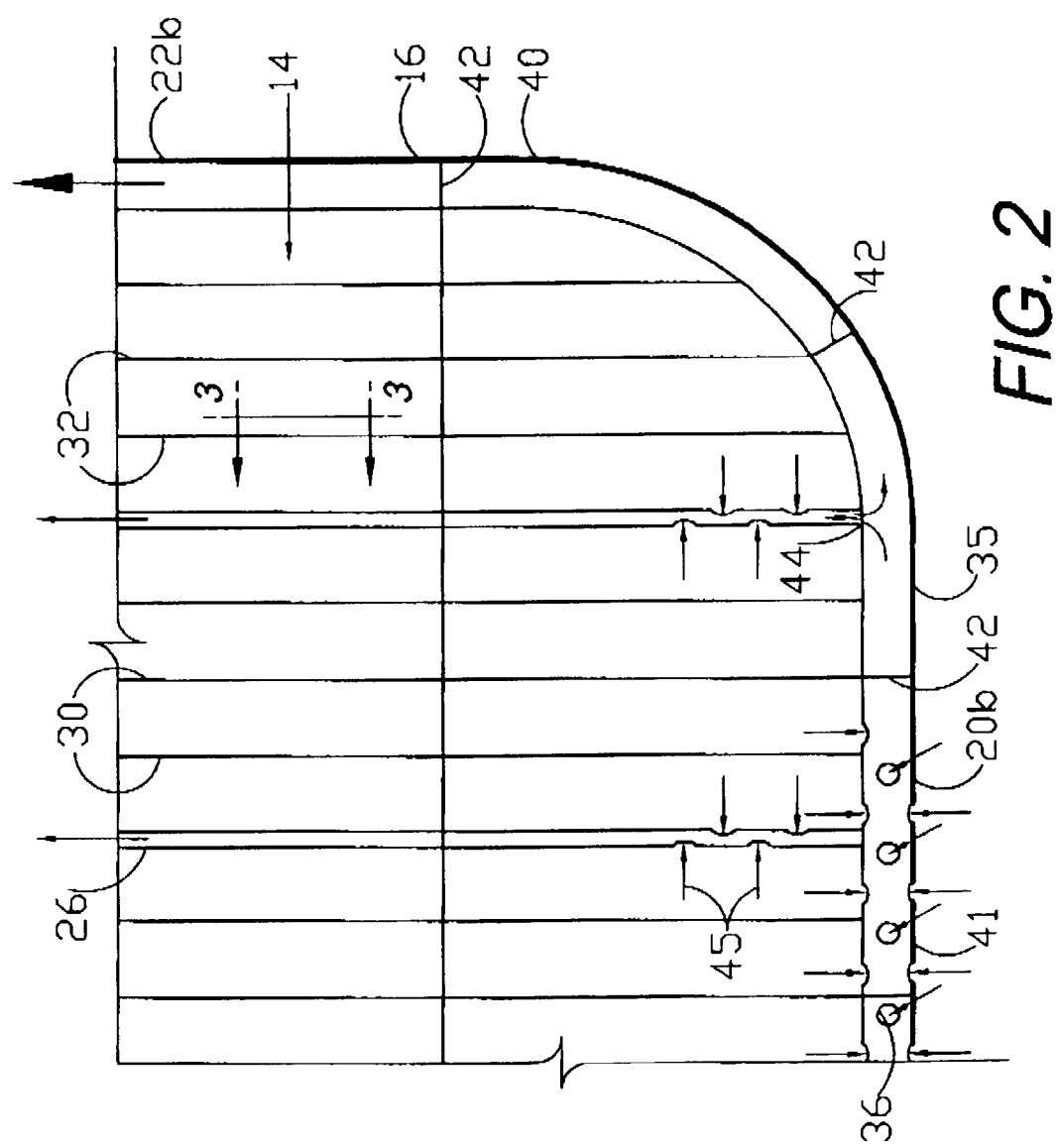
FIG. 2 is an enlarged, fragmentary, side elevational view thereof, taken generally within circle 2 in FIG. 1.

The screen 14 includes upper and lower margins 20a,b; first and second ends 22a,b; and first and second faces 24a,b. The screen 14 generally forms a grid configuration with vertical, hollow, perforated tubular risers 26 cross-connected by horizontal spacer members 28. Multiple barbed strands 30 are positioned between the risers 26. The risers 26, the spacers 28 and the strands 30 are preferably joined at their respective intersections. As shown in FIG. 3, each strand 30 includes a filament 32 with multiple, pointed barbs 34 extending upwardly and outwardly on both sides in staggered, spaced relation. The barbs 34 generally project outwardly from the screen faces 24a,b, for purposes which will be described in more detail hereinafter.

The screen or mesh 14 material can be either dissolvable (absorbable) or non-dissolvable (non-absorbable) and can be chosen from a number of commercially-available, biocompatible products, which are commonly used in medical applications for sutures, implantable meshes, and similar medical devices.

Examples of absorbable materials include, but are not limited to: aliphatic polyesters, which include, but are not limited to: homo polymers and copolymers of lactide, .epsilon.-caprolactone, p-dioxanone, trimethylene carbonate, alkyl derivatives of trimethylene carbonate, .delta.-hydroxyvalerate, 1,4-dioxepan-2-one, 1,5-dioxepan-2-one, 6,6-dimethyl-1,4-dioxan-2-one and polymer blends thereof. Examples of nonabsorbable materials include, but are not limited to: cotton, linen, silk, polyamides, polyesters, fluoropolymers, polyolefins, polyethylene and combinations thereof.

III. Screen Perimeter Member 16

The optional screen perimeter member 16 can comprise, for example, a flexible, perforated, hollow tube 35 with multiple orifices 36. As shown in FIG. 1, the tube 35 includes first and second legs 38, 40 extending generally along the screen first and second ends 22a,b, and a base leg 41 extending generally along the screen lower margin 20b. The tubing first and second legs 38, 40 terminate in respective first and second ends 38a, 40a. The tube 35 can be secured to the screen 14 by multiple ties 42, which can comprise extensions of the horizontal spacer members 28 and the strands 30. By providing dissolvable ties 42, the tube 35 can be designed for separation from the remainder of the closure screen 2 after a relatively short period of time. For example, the dissolvable material can dissolve into the patient's body after a few days, whereafter the tube 35 can be removed.

Optionally, portions of the tube 35 can be cut away from the screen 14. For example, the screen 14 can be separated along each screen end 22a,b, or it can be separated completely from the tube 35. In this manner the screen 14 and the tube 35 can be configured to accommodate a variety of conditions and tissue separation configurations.

The vertical risers 26 are optionally fluidically coupled to the tube 35 at respective T intersections 44. In this configuration the tube 35 and the vertical risers 26 cooperate to provide a manifold for fluid handling, i.e. either extraction or irrigation, as indicated by the fluid flow arrows 45.

IV. Input/Output (I/O) Subsystem 18

The input/output subsystem 18 is designed for extraction and/or irrigation of the patient's bodily fluids and/or external fluids. As shown in FIG. 1, the input/output subsystem 18 includes first and second I/O devices 18a,b attached to the tubing first and second leg ends 38a,b, which in this configuration are considered the "port" ends of the tube 35. One or both of the I/O devices 18a,b can comprise a pressure differential source, such as a VAC® (Vacuum Assisted Closure) unit available from Kinetic Concepts, Inc. of San Antonio, Tex. The use of such units for wound treatment and fluid management is disclosed in the Zamierowski U.S. Pat. Nos. 4,969,880; 5,100,396; 5,261,893; 5,527,293; and 6,071,267, which are incorporated herein by reference.

Figure 4A:
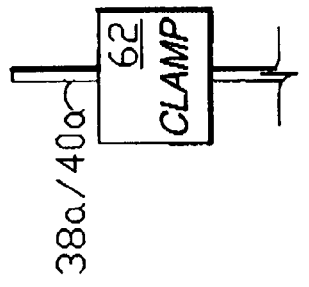
FIGS. 4a-f show alternative perimeter tube end closures comprising: 4a) subdermal termination; 4b) knotted end; 4c) Leur lock; 4d) transfer element (i.e., sponge); 4e) vacuum source; and 4f) clamped end.
Figure 4D:
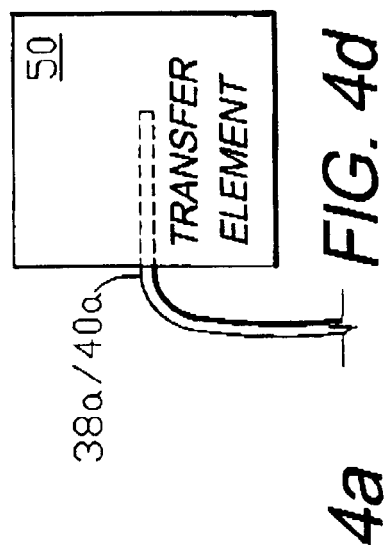
Figure 4F:
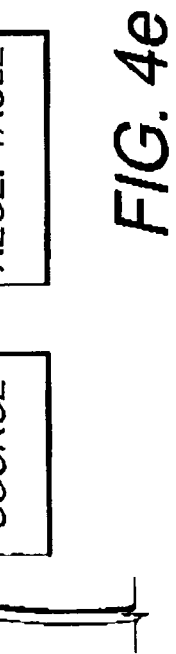
Figure 4C:
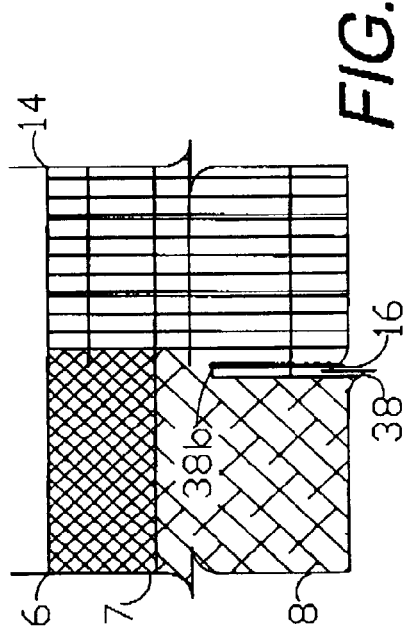
Figure 4E:
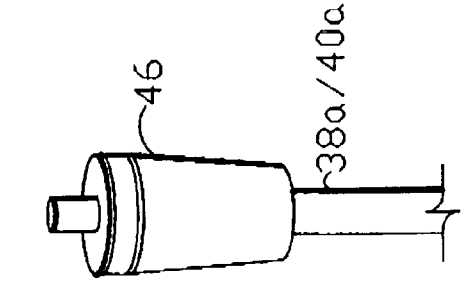
Figure 4B:
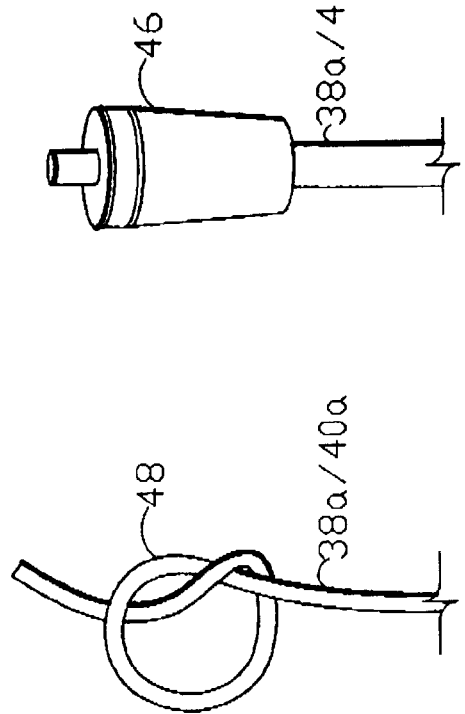

Alternatively, the tubing port ends 38a,b can be connected to various other sources of pressure differential and various drainage and irrigation devices. For example, they can be cut short below the dermis 6 and left within the separation 4 for sealing by the adjacent tissue portions 12a,b. FIG. 4a shows a truncated tubing end 38b. The tubing ends 38a/40a can be knotted (as shown at 48 in FIG. 4b), clipped, tied (e.g., with a suture) or otherwise closed off either above or below the dermis 6. FIG. 4c shows a Leur lock coupling 46 mounted on a tubing end 38a/40a. Still further, a transfer element comprising a piece of foam or sponge 50 can be coupled to the tube 35 at an end 38a/40a (FIG. 4d). Examples of such foam and sponge materials and configurations are discussed in the Zamierowski U.S. patents identified above. A pressure differential source, such as a vacuum source 51, can be connected to a tube end 38a/40a and to a fluid receptacle 66, as shown in FIG. 4e. A clamp 62 is shown in FIG. 4f and closes the tube end 38a/40a. The clamp 62 can be chosen from among several suitable clamps, which are commonly used for medical applications.

Either tube end 38a/40a can function as either an inlet port or an outlet port with respect to the system 2. For example, suction can be applied for pulling fluid from the patient through the system 2 through either tube end 38a/40a. Still further, fluid can be pulled in both directions through the system 2 by alternately or jointly applying suction to the tube ends 38a/40a. For example, suction can be simultaneously applied to both tube ends 38a/40a.

V. Operation And Closure Method

Figure 5B:
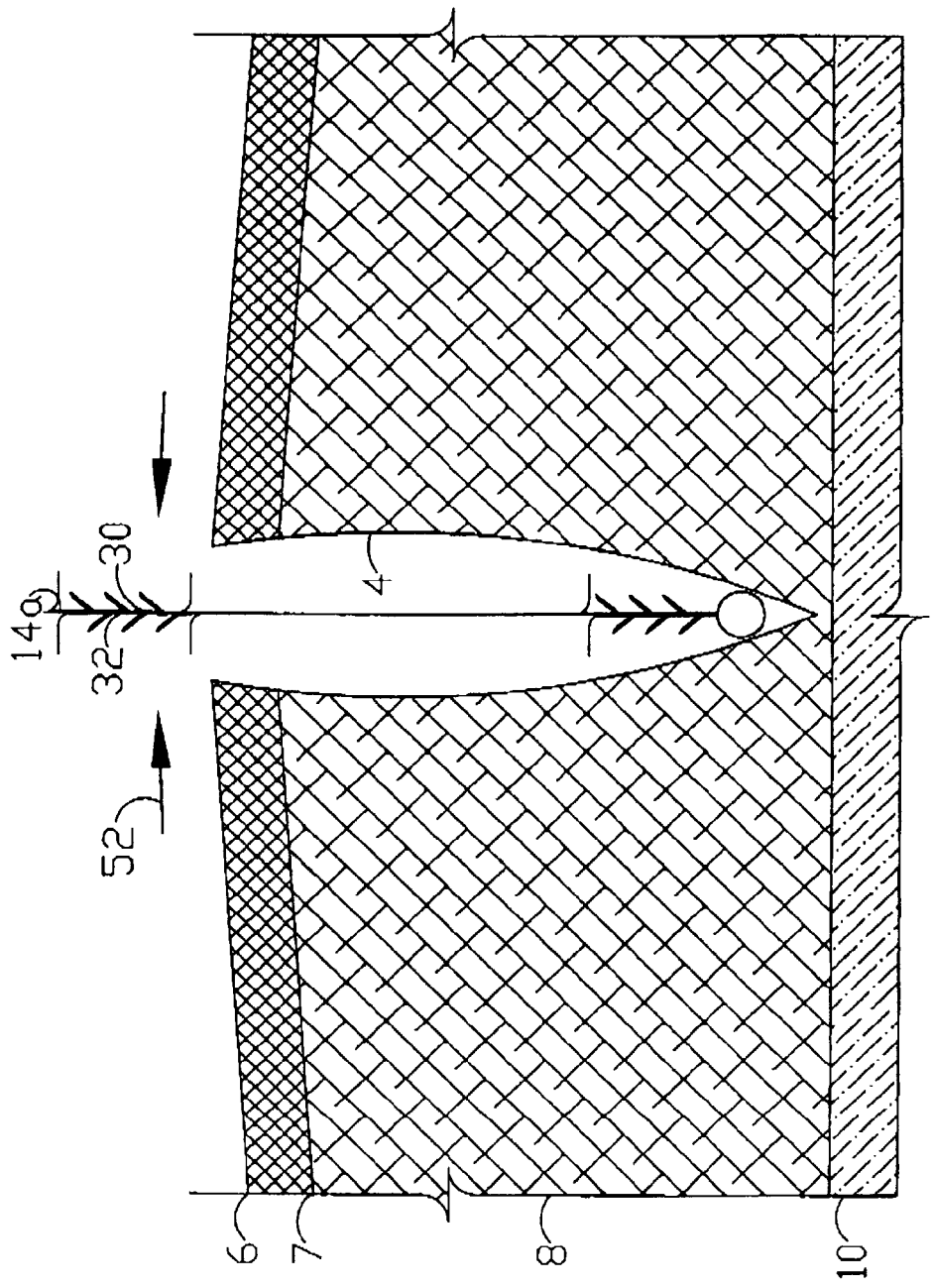
Figure 5C:
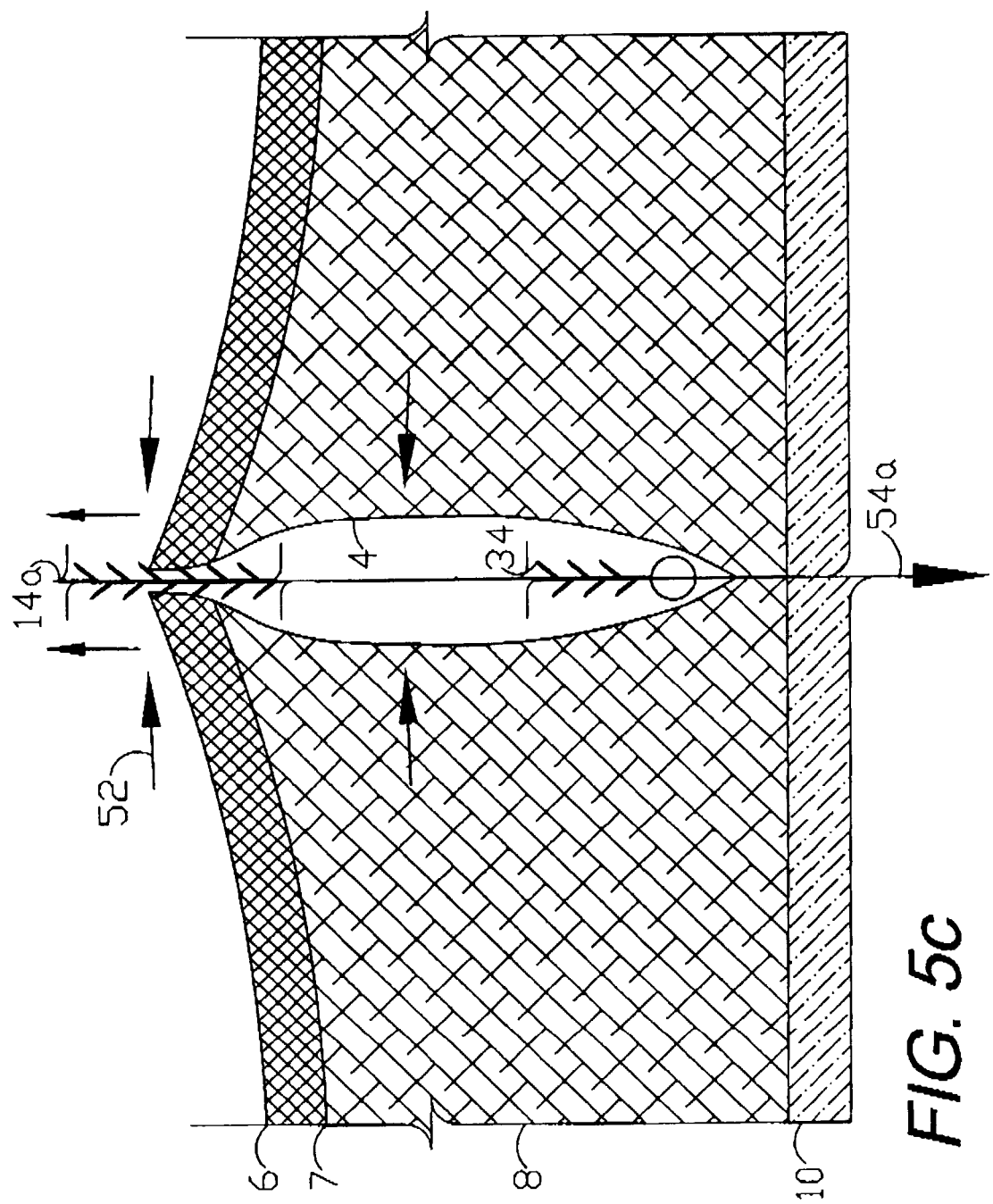
Figure 5D:
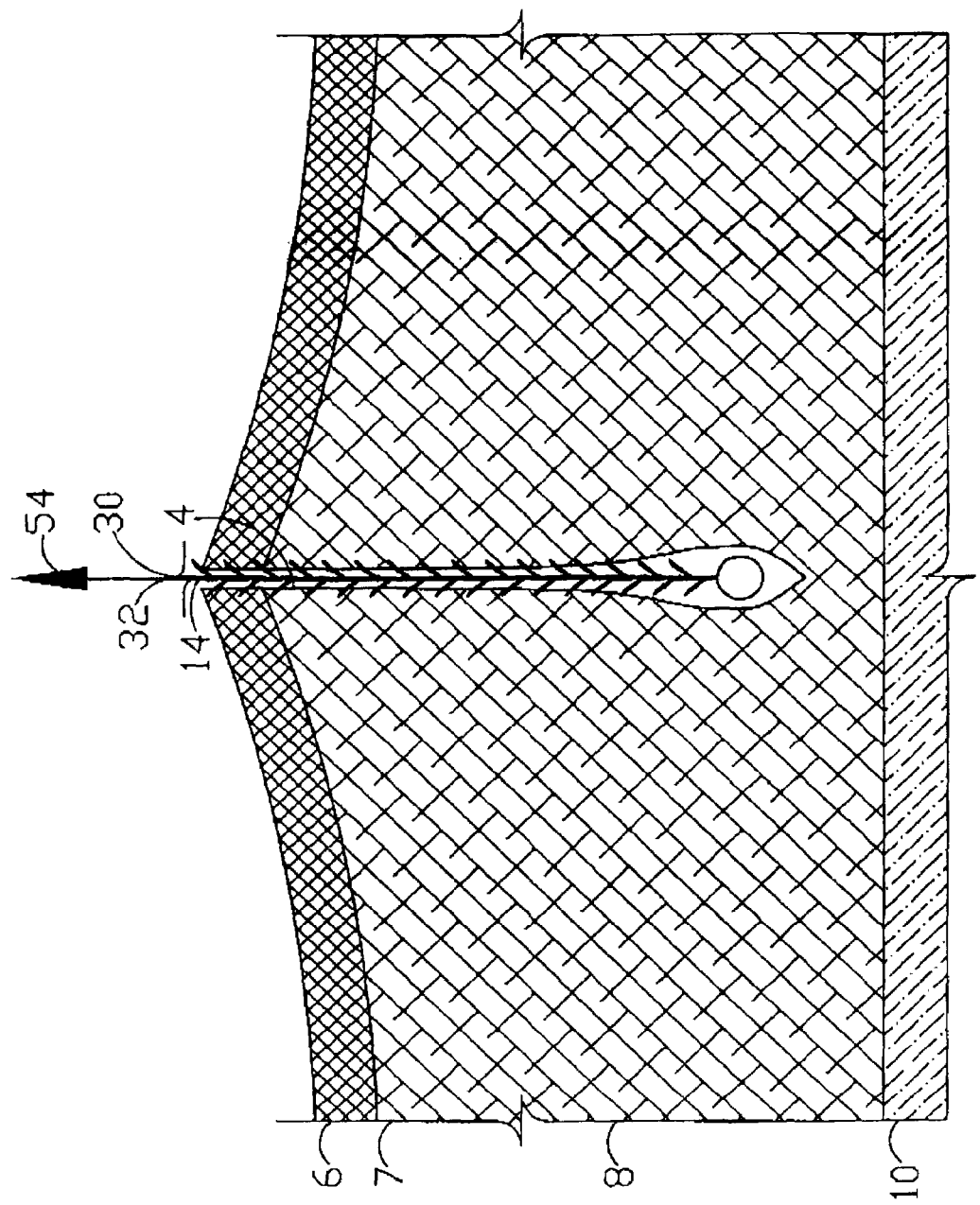

FIGS. 5a-e show an installation methodology utilizing the system 2 of the present invention. In FIG. 5a, the closure screen 2 is placed in the separation 4 with the tubing base 41 located at the bottom of the separation (e.g., wound or incision) 4 and in proximity to the fascia layer 10. As shown, the tissue portions or wound/incision edges 12a,b are spaced apart. The screen upper margin 20a can protrude outwardly from the dermis 6. FIG. 5b shows the tissue separation edges 12 being pushed together as indicated by the force arrows 52. FIG. 5c shows the separation edges 12 engaged at the dermis 6, and spaced apart somewhat within the subcutaneous layer 8. The edges 12 can be pushed together as indicated by the force arrows 52. Moreover, the screen 2 can be held or positioned inwardly in order to advance the barbs 34 in the separation edges 12, as indicated by the inward or downward force arrows 54a. FIG. 5d shows the separation edges 12a,b substantially closed on the screen 2. Tugging on the screen 14 in the general direction of the outward force arrow 54b sets the mesh barbs 34.

Figure 5E:
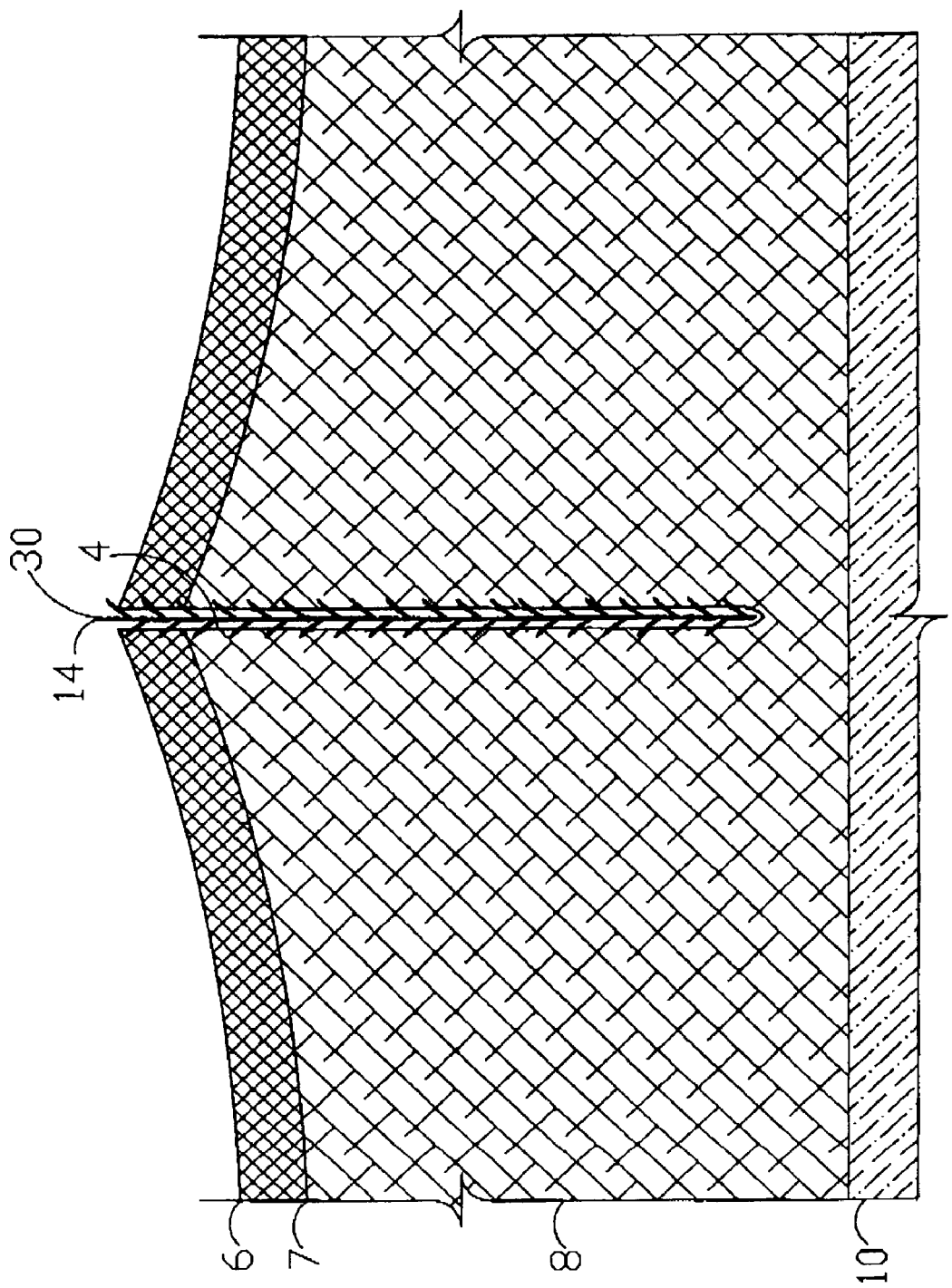

FIG. 5e shows the separation 4 closed on the closure screen 2, with the tubing 35 removed from the screen 14.

The tubing 35 can be removed either pre-installation by cutting the ties 42, or post-installation by allowing the ties 42 to dissolve, whereafter the unsecured tubing 35 can be extracted.

FIG. 6a shows the barbs 34 compressed by engagement with the separation edges 12a,b. As shown, the separation edges 12 can be manually closed by pressing along the horizontal force arrows 52. The barbs 34 thus deflect inwardly due to their flexibility, thereby allowing the separation edges 12a,b to slide upwardly or outwardly along the screen 14. This process can be repeated until the separation 4 is closed, as shown in FIG. 6b. Any protruding length of the screen 14 can be cut close to the dermis 6. In the final configuration (FIGS. 5e and 6b), the barbs 34 are embedded in the tissue adjacent to the separation edges 12a,b and thus secure the separation 4 in a closed position. The fluid conducting properties of the screen 14 facilitate extracting fluid. An outward or upward force arrow 54b indicates a force direction whereby the screen barbs 34 are set in the adjoining tissue. It will be appreciated that the screen 14 can be securely set in place with the barbs 34, yet the separation edges 12a,b will remain capable of sliding up on the screen 14 by disengaging the barbs 34 with lateral forces, as shown in FIG. 6a. Skin hooks 55 can be used for engaging the tissue portions 12a,b and tugging same outwardly as shown in FIG. 6a. The skin hooks 55 can facilitate positioning and repositioning the screen 14.

VI. Alternative Embodiment Closure Screen Systems and Methodologies

Figure 7A:
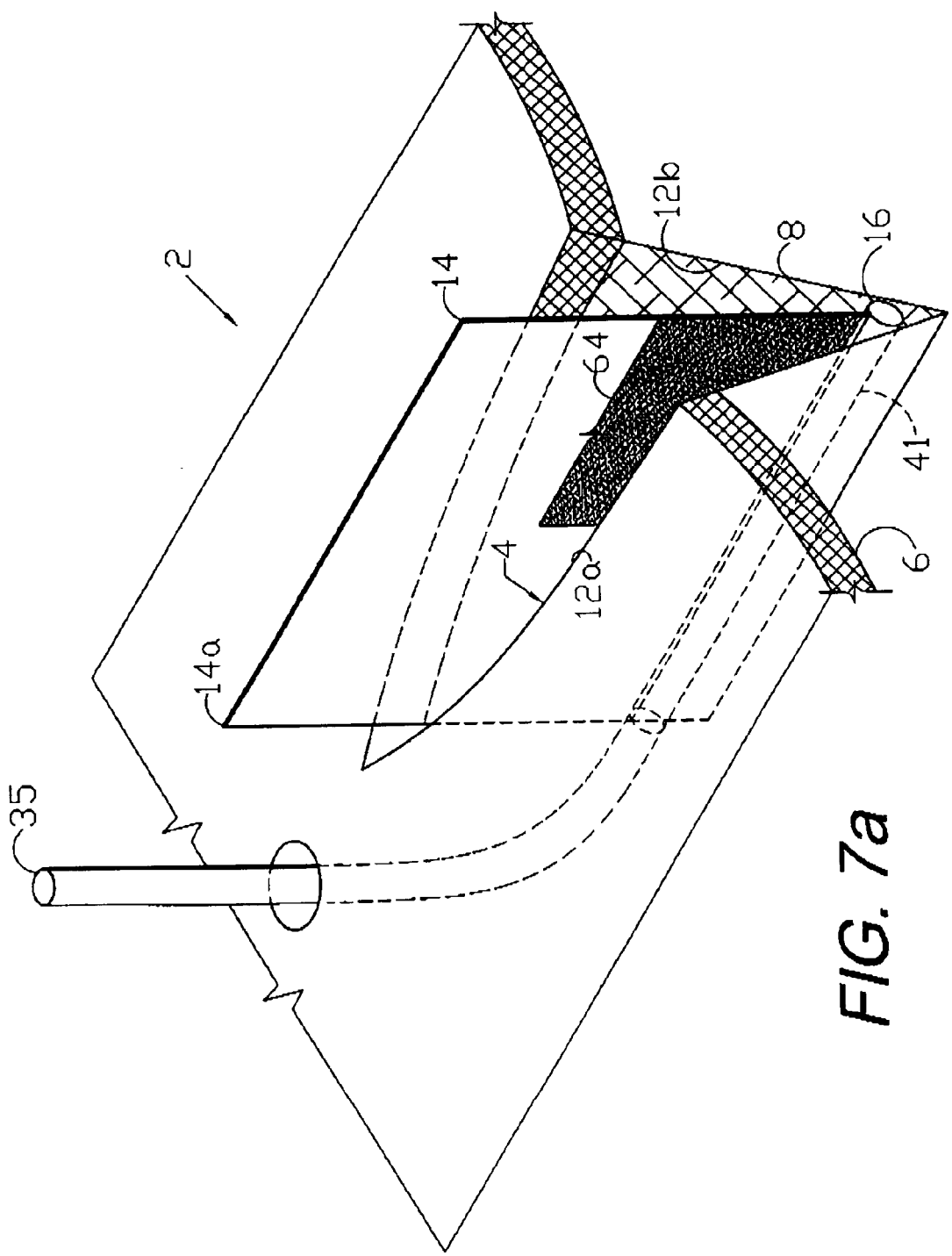
Figure 7B:
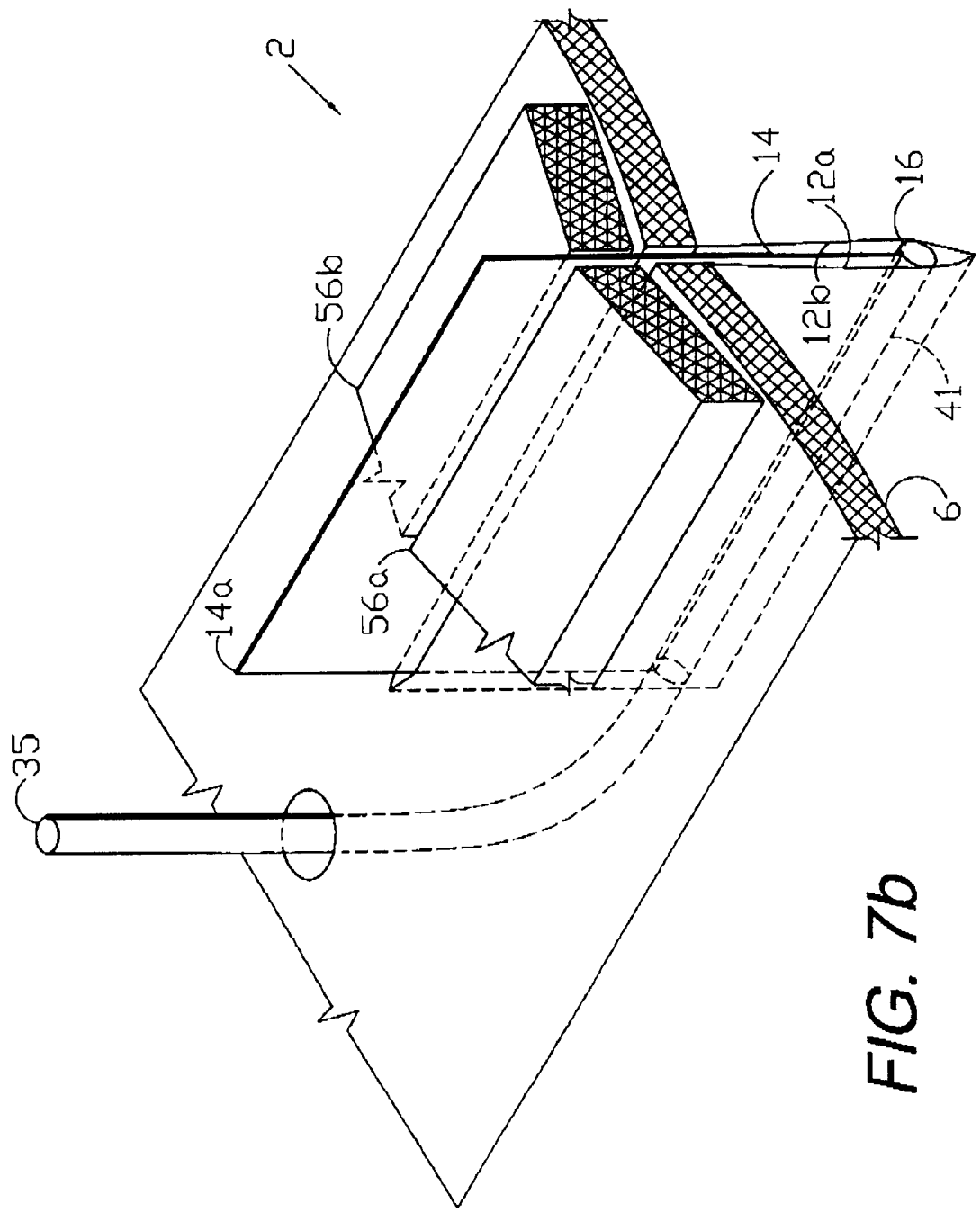

FIGS. 7a-f show an alternative procedure for mounting the closure screen 2 in a wound drainage application utilizing pressure differential. As shown in FIG. 7a, the tubing 35 can pass through the tissue adjacent to the wound 4 and exit the dermis 6 for termination of the tubing end 38a/40a as described above. An optional layer of a suitable, biocompatible adhesive 64 is shown applied to the closure screen first face 24a for securing same to the first wound edge 12a. FIG. 7b shows the screen 14 extending upwardly from the dermis 6 with the wound edges 12a,b brought together in a manner similar to that described above.

Figure 7C:
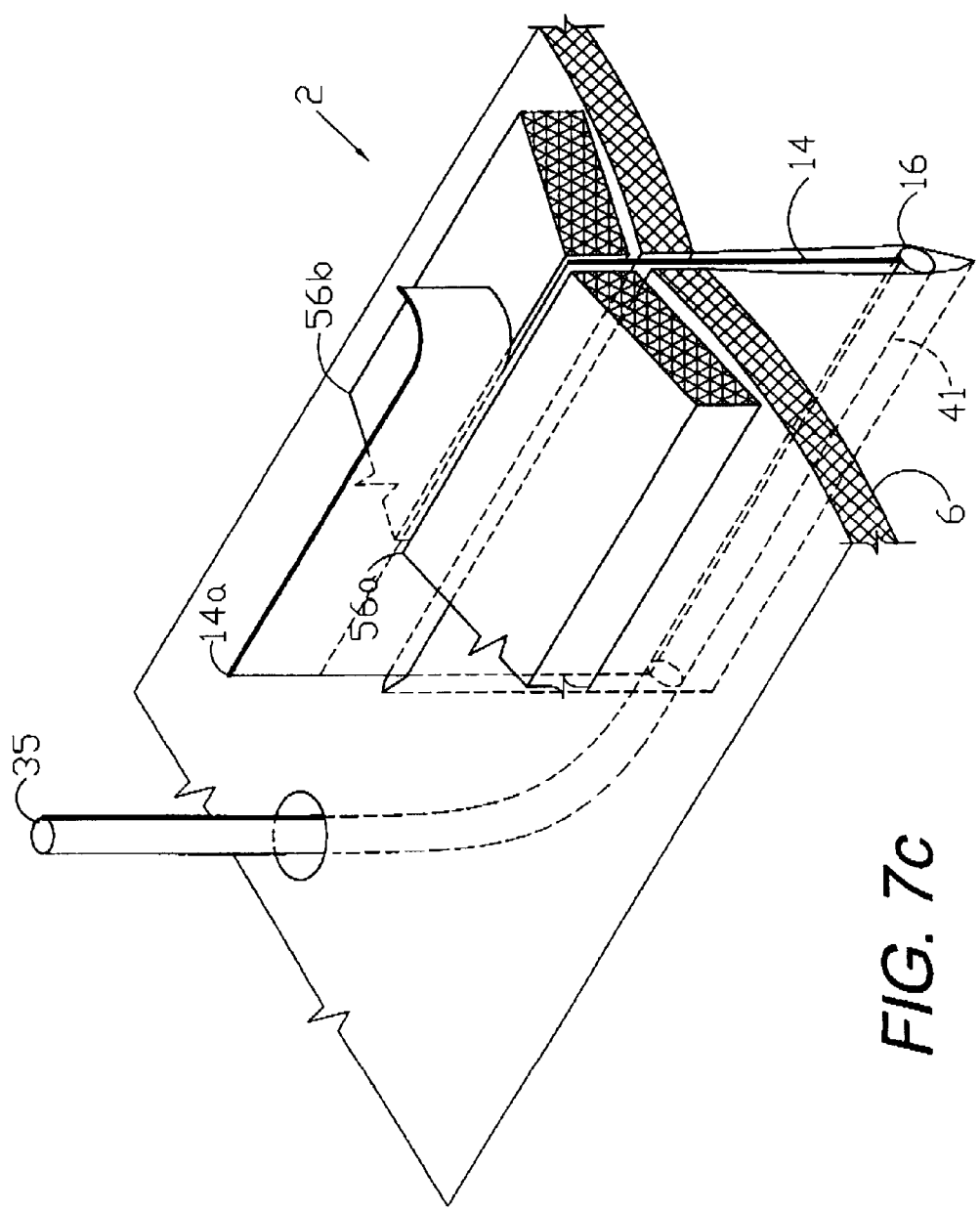
Figure 7D:
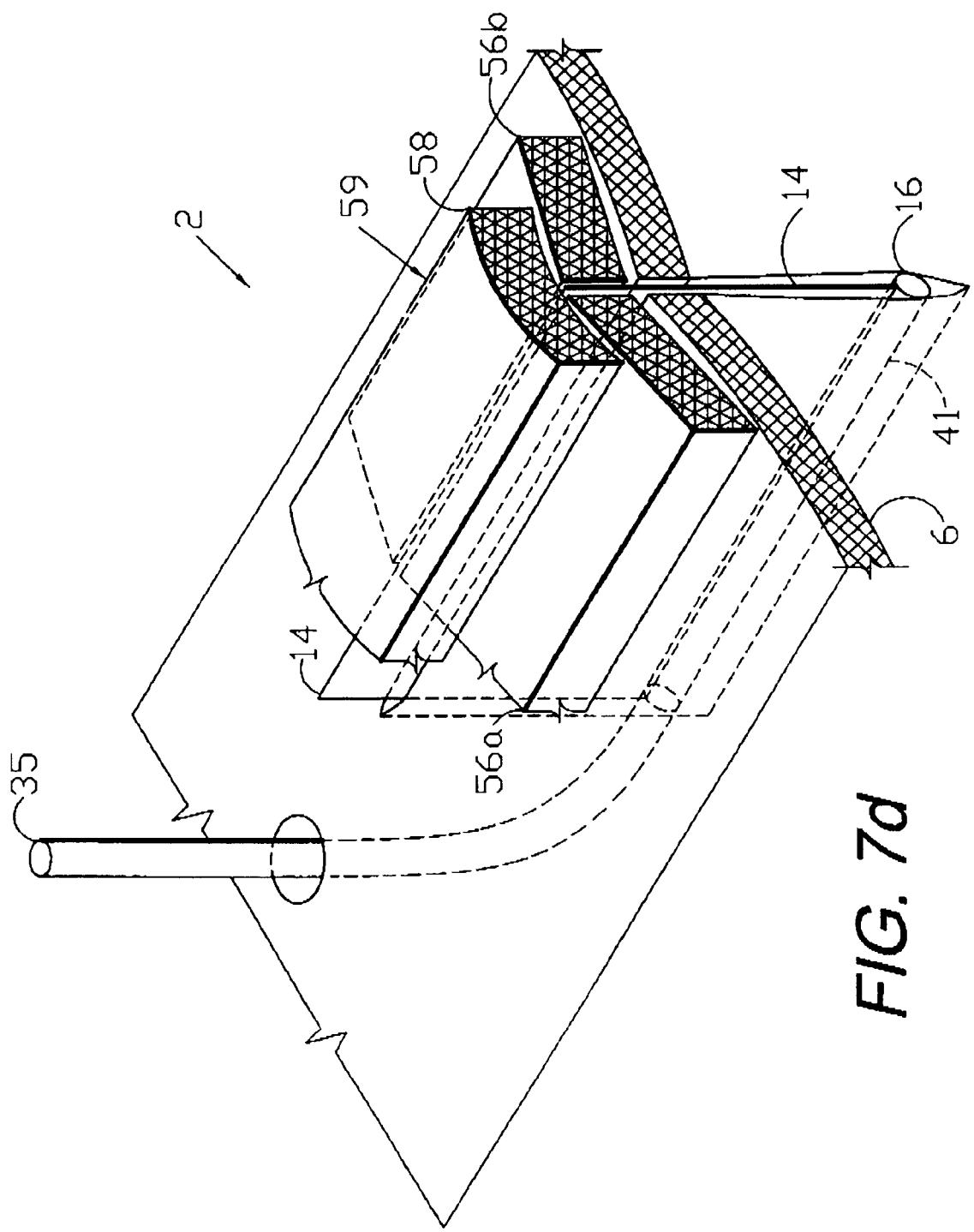

The input/output subsystem 18 includes a pair of optional fluid transfer elements comprising foam or sponge members 56a,b placed on the dermis 6 on either side of a protruding portion 14a of the screen 14. The screen 14 is then cut to a level generally flush with the upper surfaces of the sponges 56a,b, as shown in FIG. 7c. An optional sponge bridge 58 is placed over the sponge members 56a,b (FIG. 7d). Examples of suitable transfer element materials are discussed in the Zamierowski patents noted above and include open-cell, porous foam materials (e.g., polyurethane ester (PUE)) chosen for their hydrophobic properties and passage of liquids. Polyvinyl acetate (PVA) material can be used for its hydrophilic properties. The transfer element subassembly 59 formed by the sponge members 56a,b and 58 can be connected to a vacuum source, a fluid irrigation source, etc. Moreover, it can be connected to additional fluid transfer elements and covered with various flexible membranes and drapes, which can be semi-permeable or impervious, as indicated for the closure and treatment of particular separations and wounds.

FIG. 7e shows a tubing placement tool 120 with a handle 122, a shaft 124 and a hook 126 terminating at a pointed or rounded, bullet-shaped tip 128. FIG. 7f shows the tool 120 passing tubing 35 through tissue in the subcutaneous layer 8 and into proximity with the dermis 6. The tip 128 is received in a blind end 134 of the tubing 35 through a notch 136 formed therein. The thrust of the tool 120 causes tenting of the dermis 6, as shown at 138, whereat the dermis 6 can be opened with a scalpel 140 and the tubing 35 can exit the patient for suitable termination arrangements, such as those shown in FIGS. 4a-f above.

Figure 8:
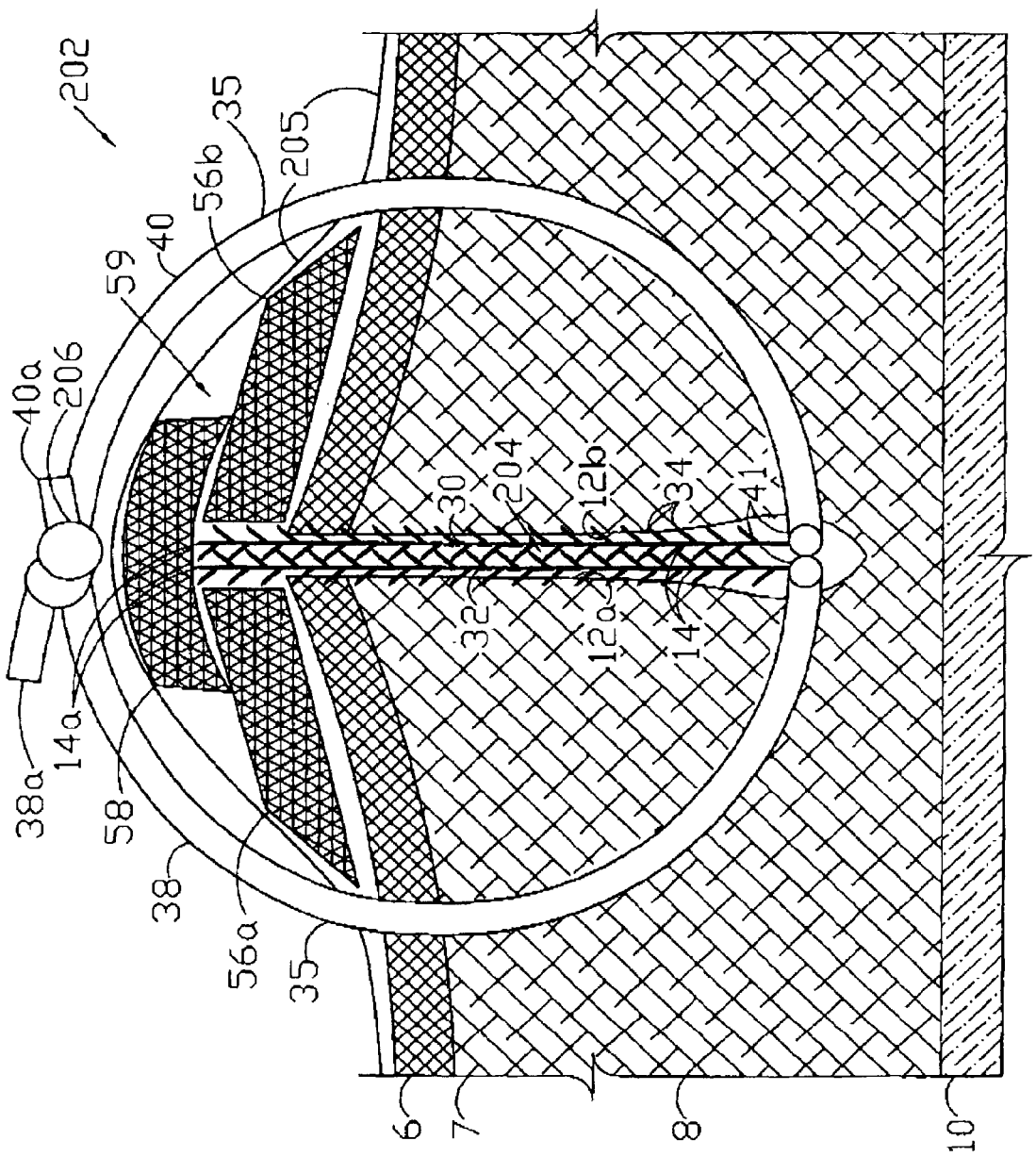
FIG. 8 is a cross-sectional view of a tissue separation closure utilizing tubing for securing the closure screen with a fluid transfer subassembly connected to an upper edge of the closure screen.

FIG. 8 shows a modified embodiment closure system 202 with a pair of screens 14 positioned generally end-to-end in a separation 204. A transfer element subassembly 59 is placed over the separation 204 and a membrane drape 205 is placed thereover. The tube 35 is passed through tissue on either side of the separation 204 (e.g., using the procedure and the tubing placement tool 120 described above) and exits the dermis 6 on either side of the transfer element subassembly 59. The tube 35 lengths are knotted at 206. The tube 35 lengths thus function as sutures or retainers for securing the closure system 202 in the separation 204. The tube ends 38a or 40a can be utilized for this purpose, thus leaving the other tubing ends available for fluid communication with one or more of the input/output subsystems 18 described above.

The tube 35 can be secured by suitable fasteners, such as clips and the like, located above the dermis 6. Moreover, the screens 14 can be overlapped, abutted, spaced slightly and otherwise configured and positioned as necessary for particular tissue separations. Still further, the screens 14 are adapted to be trimmed as necessary.

FIG. 9 shows a modified embodiment tubing/suture subassembly 220 with a needle 222 including a sharpened, distal end 224 and a proximate end 226 with multiple, annular ridges 226a. A length of flexible tubing 228 combines the functions of screen perimeter member and suture. The flexible tubing 228 terminates at an end 228a adapted for releasably mounting on the needle proximate end 226, whereat it is retained in place by the ridges 226a. The tubing 228 is optionally connected to the screen 14 as described above and can include perforations 228b for fluid drainage and/or irrigation in conjunction with input/output subsystems 18, also as described above. The tubing/suture subassembly 220 is adapted for securing the screen 14 in place and for closing the separation 4 by passing the tubing 228 through adjacent tissue. The tubing/suture subassembly 220 and the screen 14 can be prepackaged and presterilized for closing and treating separations, which can include wounds and incisions.

Figure 11B:
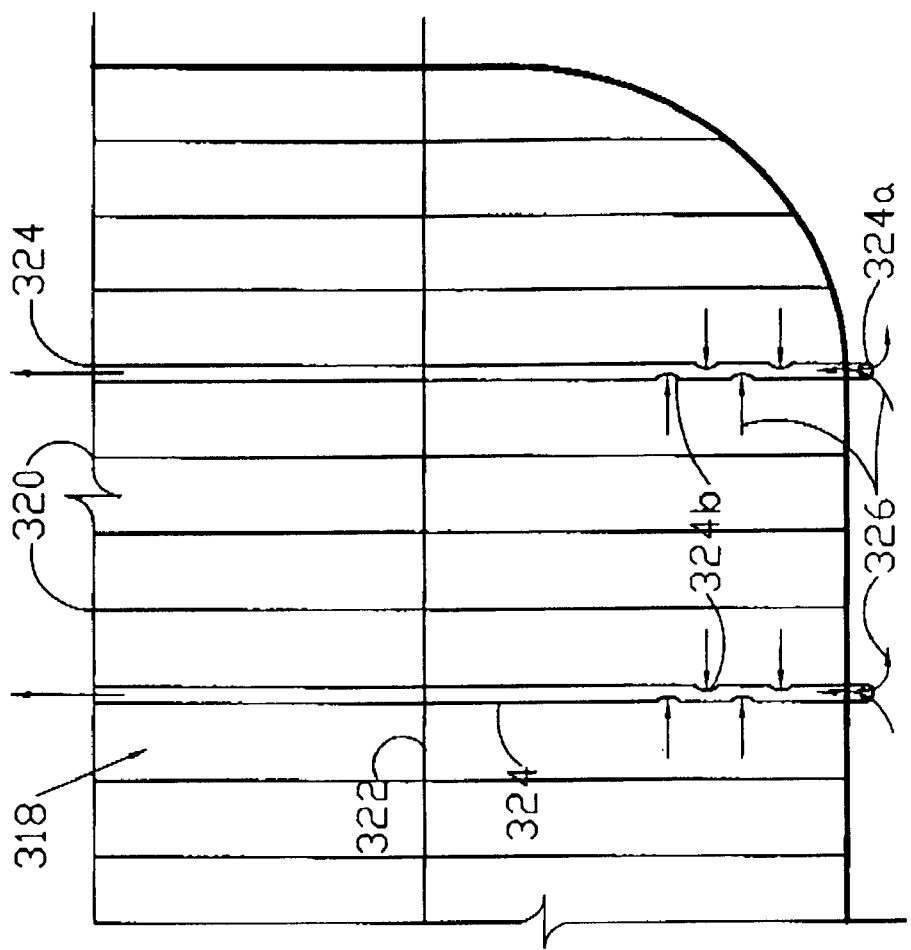
FIG. 11b is an enlarged, fragmentary, side elevational view thereof, showing modified vertical risers.
Figure 11A:
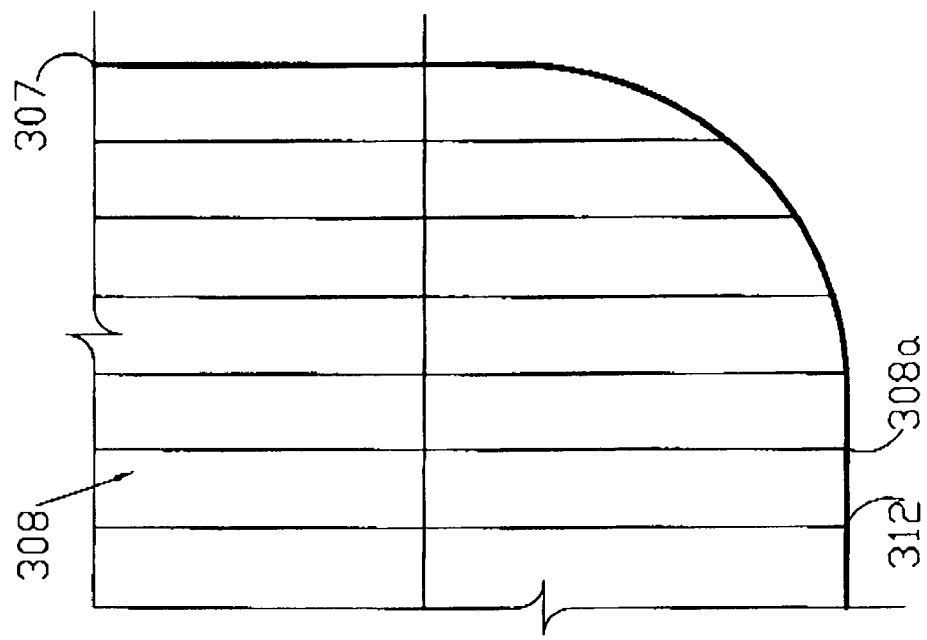
FIG. 11a is an enlarged, fragmentary, side elevational view thereof, taken generally within circle 11a in FIG. 10.

FIGS. 10, 11a and 11b show modified embodiment closure screen systems 302 with first and second suture subassemblies 304, 306 comprising the screen perimeter member. The suture subassemblies 304, 306 include respective curved needles 304a, 306a which are swaged or adhesively connected to opposite ends 304b, 306b of a common length of suture thread 307. The suture thread 307 can be absorbable or nonabsorbable. As shown in FIG. 10, the screen closure system 302 can be preassembled with the suture thread length 307 releasably secured to the perimeter 308a of a screen 308. Prior to installation of the screen 308, the suture 307 can be disconnected or severed therefrom, either partly or completely. For example, the suture 307 can be separated along the screen ends 310a, 310b respectively, thereby leaving the suture thread lengths secured only along a screen lower margin 312.

In operation, the suture subassemblies 304, 306 facilitate installation of the suture/screen closure system 302, thereby providing a preassembled device which incorporates the necessary components for securing same in a separation 4. For example, the screen 308 can be secured at the bottom alone by passing the suture subassemblies 304, 306 through tissue portions located at the bottom of the separation 4.

Alternatively, the suture subassemblies 304, 306 can be passed through the adjacent tissue and exit the surface of the dermis 6, whereby the suture subassemblies 304, 306 can be used for closing the separation 4 at the dermis 6. Barbed strands 320 can interact with the tissue portions 12a,b as described above, whereby the screen 308 provides a relatively secure mechanical connection between the separated tissue portions 12a,b. The suture subassemblies 304, 306 can be utilized for various purposes in the separation 4, including attachment and tacking of the dermis 6, the deep dermal layer 7, the subcutaneous layer 8 and the fascia 10. Still further, all or part of the suture subassemblies 304, 306 can be removed, and additional suture subassemblies can be mounted on or sutured to the screen 308.

FIG. 11a shows the screen 308 attached to the suture thread 307. FIG. 11b shows an alternative construction screen 318 with hollow tubular vertical risers 324 located between adjacent, respective vertical strands 320, all connected by the spacers 322 and adapted for communicating fluid with the separation 4 through the open riser ends 324a and the perforations 324b, as indicated by the fluid flow arrows 326. All or part of the screen/suture system 302 can comprise absorbable material.

Figure 13B:
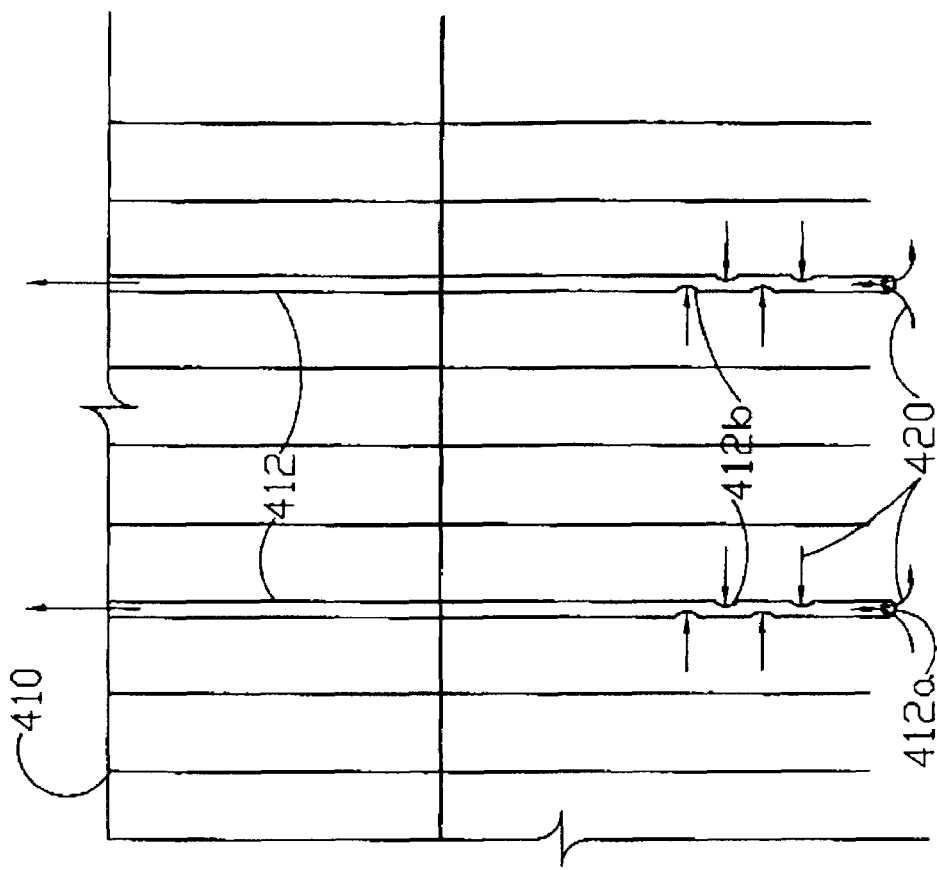
FIG. 13b is an enlarged, fragmentary, side elevational view thereof, showing modified vertical risers.
Figure 13A:
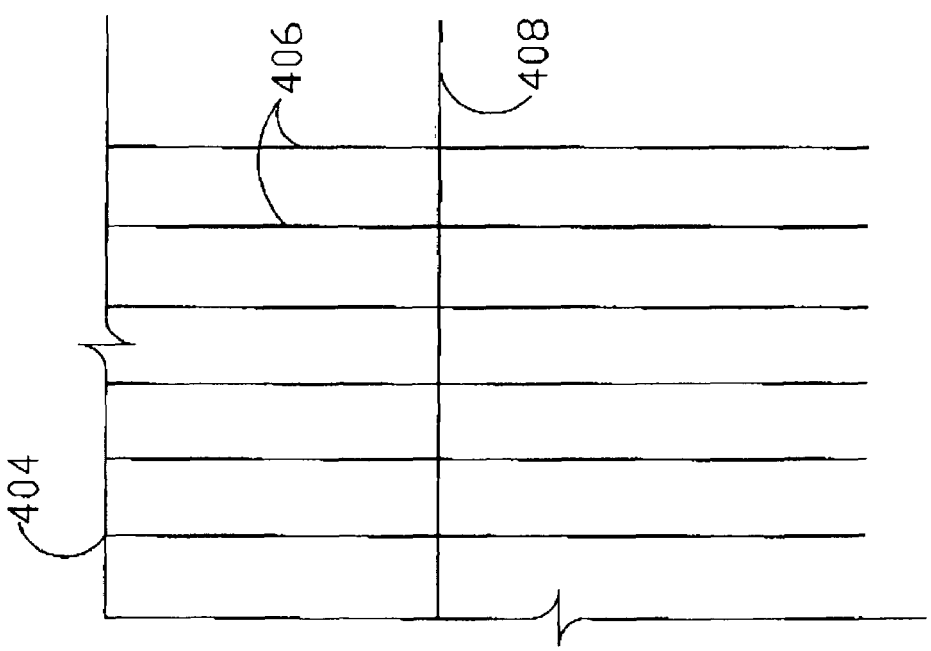
FIG. 13a is an enlarged, fragmentary, side elevational view thereof, taken generally within circle 13a in FIG. 12.

FIGS. 12, 13a and 13b show a modified embodiment screen-only closure screen system 402 and application methodology. A screen or mesh 404, similar to the screen 14 with barbed strands 30 described above, is placed in a separation 4 against the first tissue portion 12a. The second tissue portion 12b is then placed against the screen 404 whereby the separation 4 is closed and can be secured by the mechanical action of the screen 404. The screen 404 can be supplemented with sutures, drainage tubing, I/O devices, and other auxiliary components for purposes of closing the wound edges 12, draining the inside of the tissue separation 4, fighting infection, pain management and all other functionalities associated with the present invention, as discussed elsewhere herein. For example, the screen 404 can be secured with sutures at the subcutaneous level 8. Various fluid interconnecting devices can be utilized as necessary, and can be designed for removal after they serve their initial purpose. External drainage can also be achieved at the dermis level 6 utilizing transfer element subassemblies, such as the example designated 59 and described above (FIG. 7d). Moreover, drainage and irrigation tubing can be installed within the wound 4 alongside or adjacent to the screen 404. It will be appreciated that a screen-only version of the invention can comprise various suitable biocompatible absorbable and non-absorbable materials, including the materials disclosed above.

FIG. 13a is an enlarged view of the screen 404 and particularly shows barbed strands 406 and horizontal spacers 408, which are connected together in a grid pattern forming the screen 404. FIG. 13b shows an alternative embodiment with a modified screen 410 including vertical risers 412 comprising hollow tubing, which are connected to and spaced by horizontal spacers 408. Fluid flows into and out of the vertical risers 412 through open riser ends 412a and perforations 412b, as indicated by the fluid flow arrows 420.

Figure 14A:
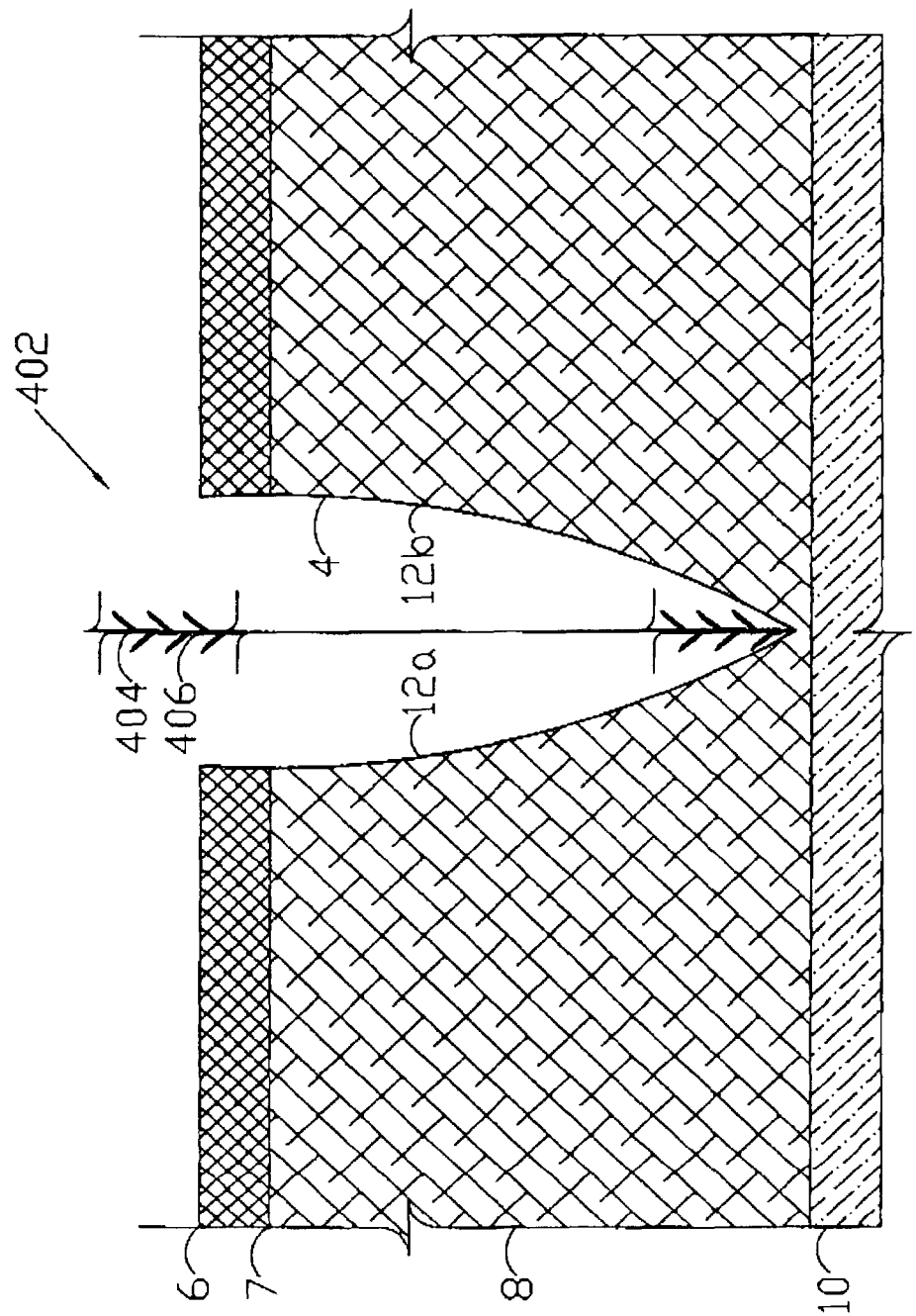
Figure 14B:
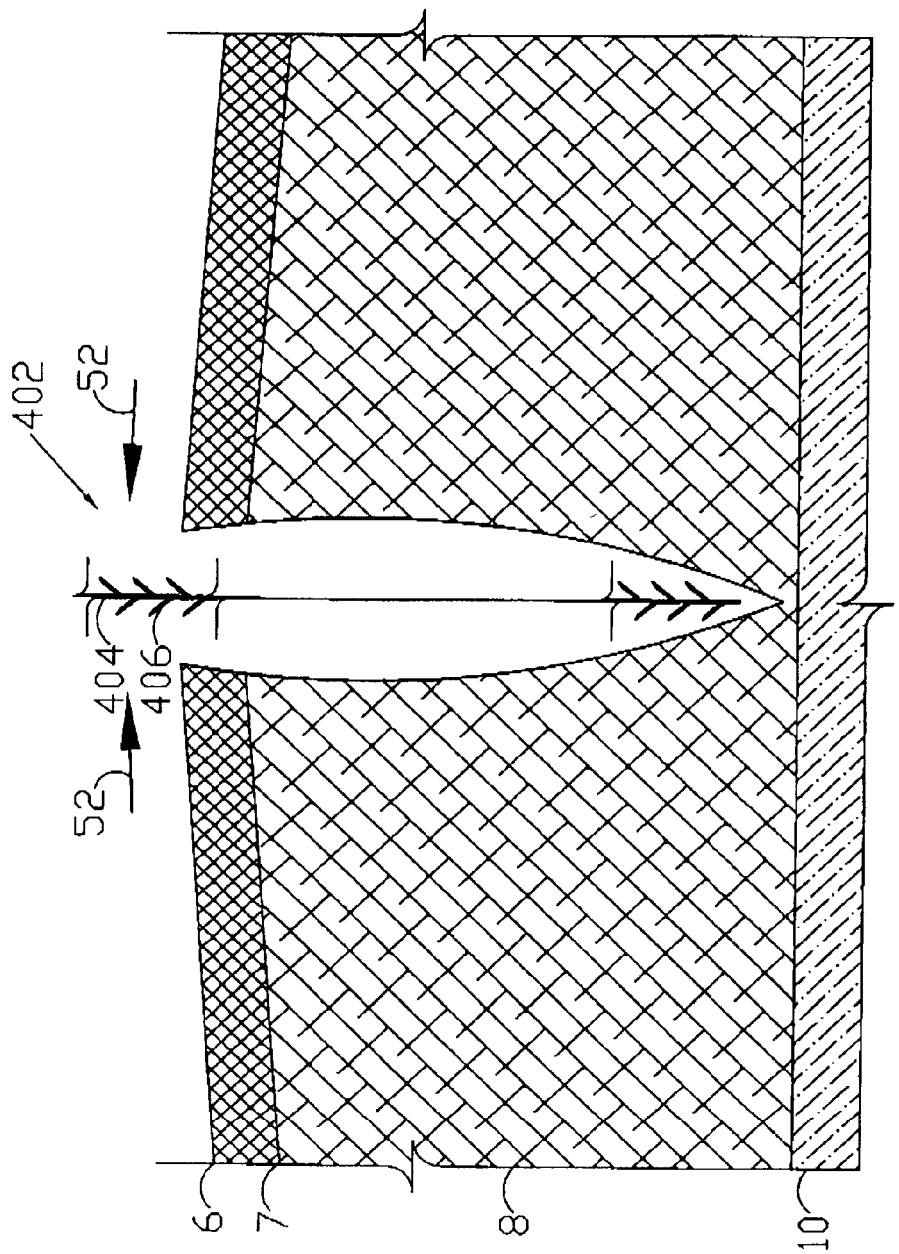
Figure 14C:
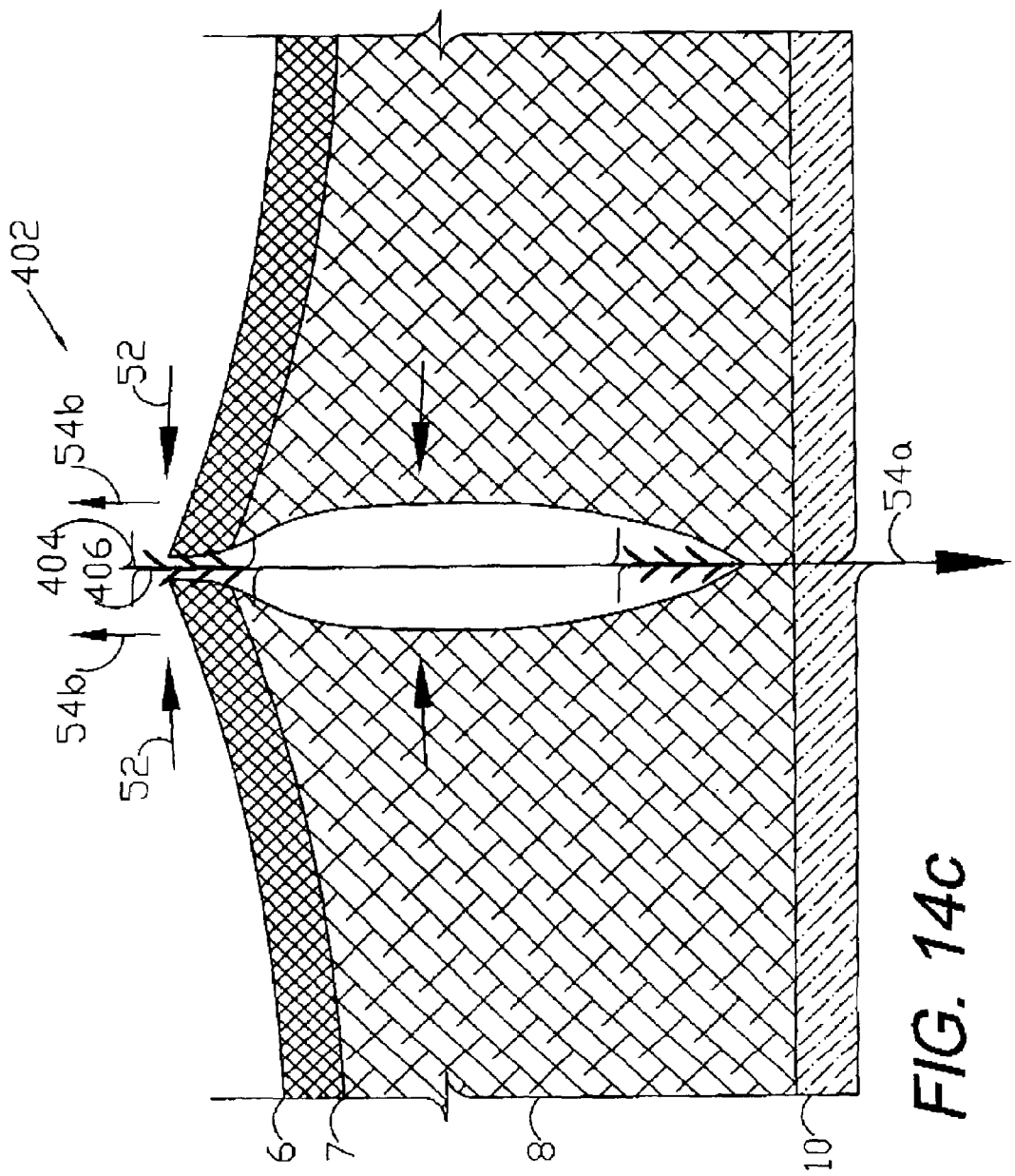
Figure 14D:
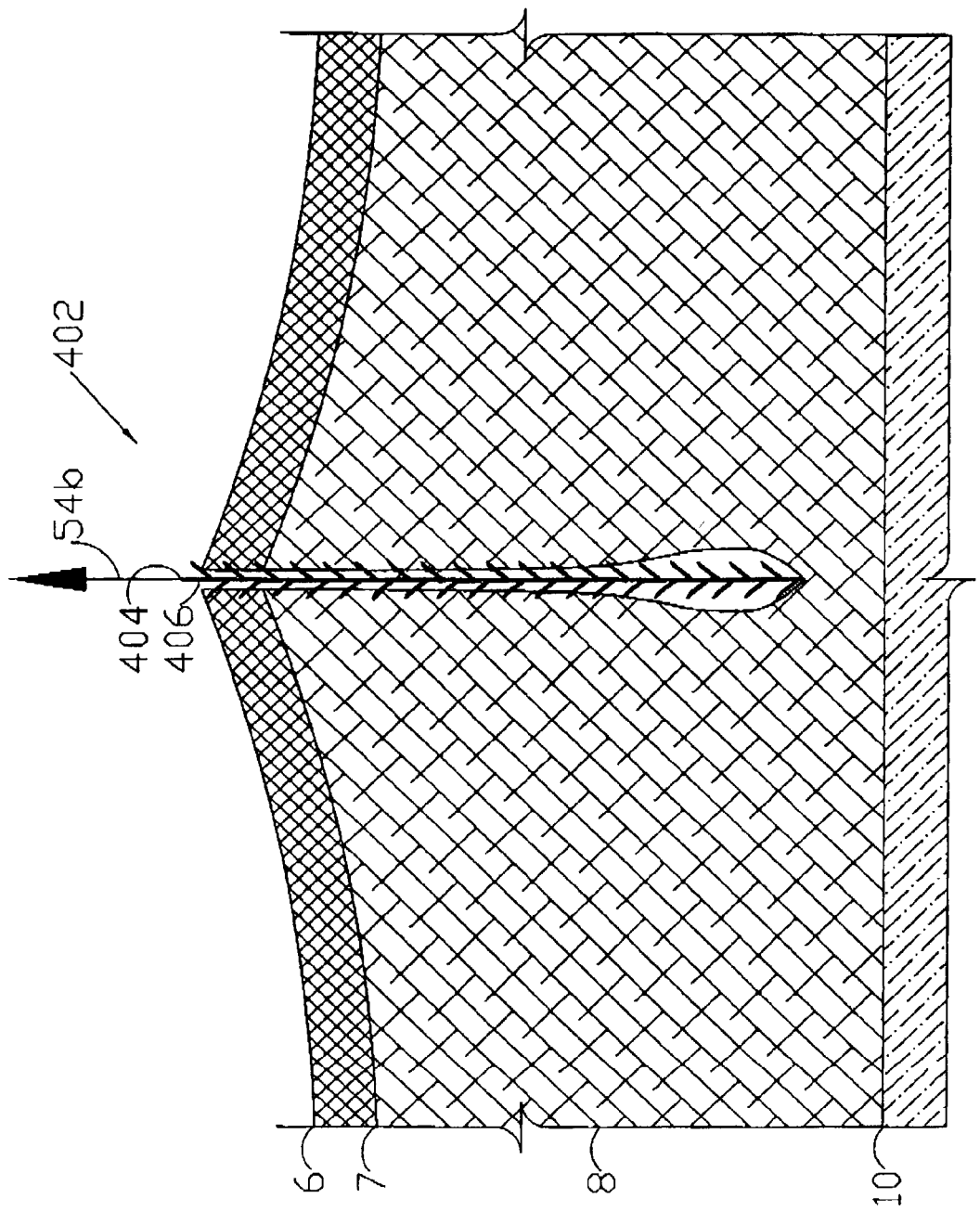
Figure 14E:
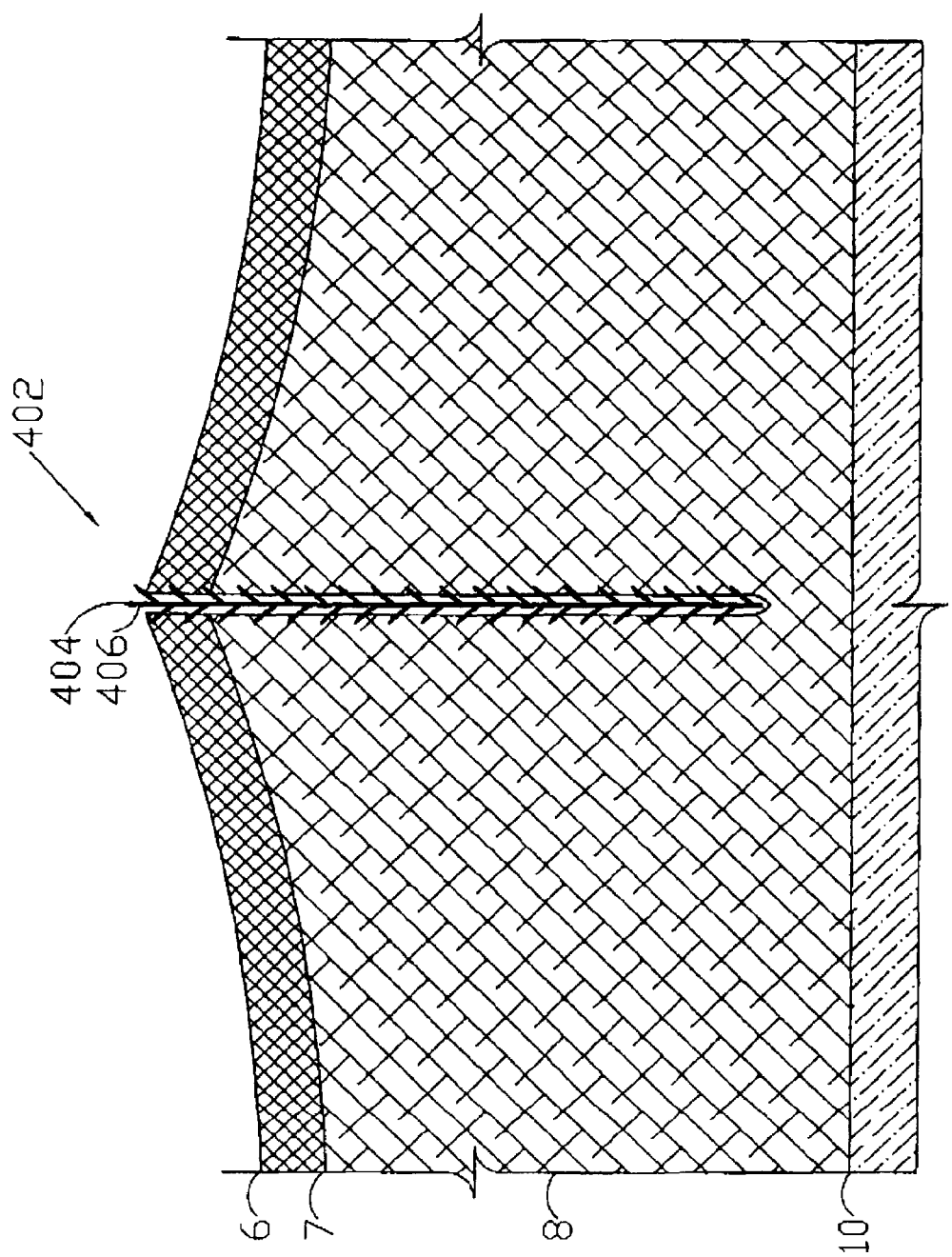
Figure 14F:
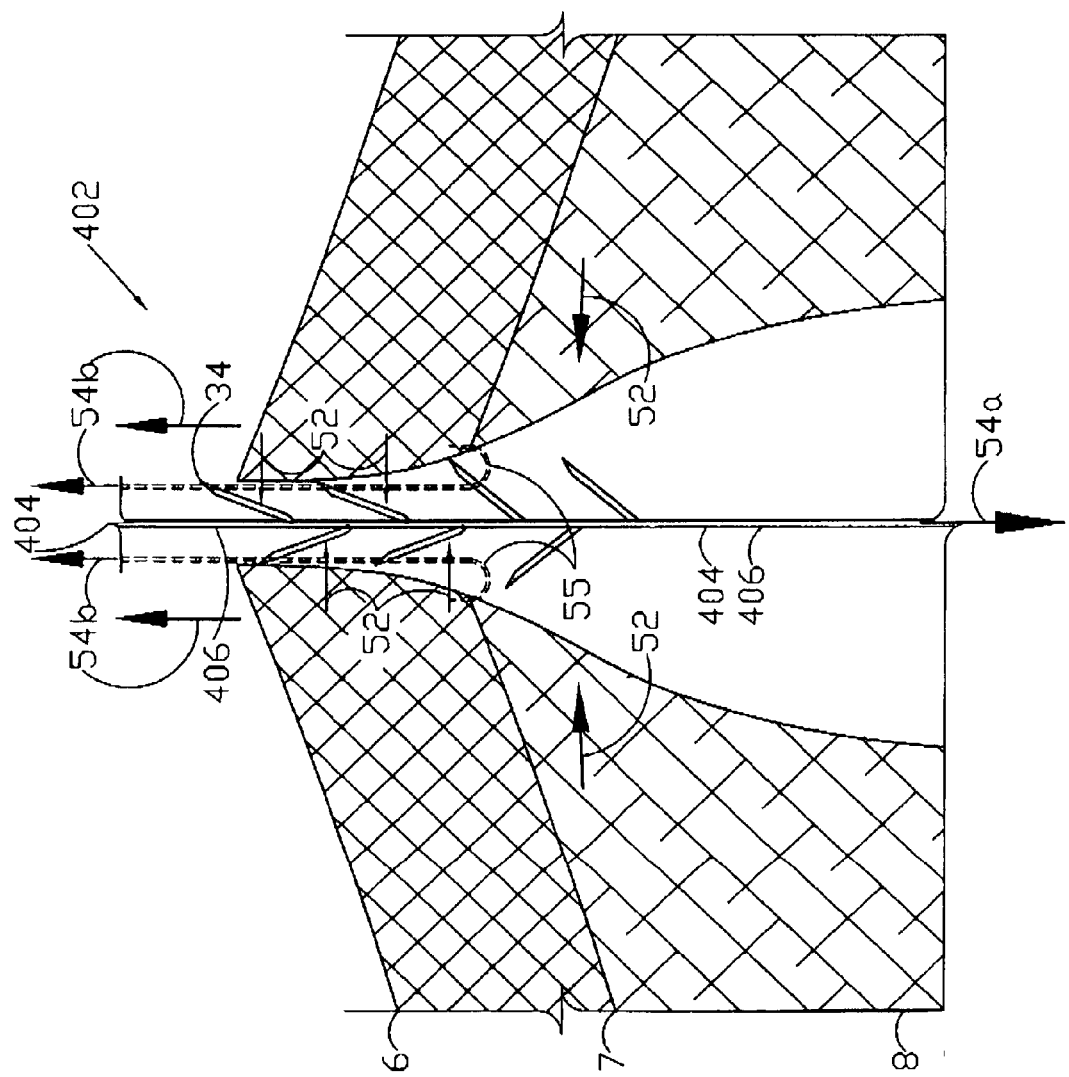

FIGS. 14a-g show the screen 404 installed in a tissue separation 4 and closing same, utilizing the methodology of the present invention. The methodology shown in FIGS. 14a-g is similar to the methodology shown in FIGS. 5a-e and 6a,b. FIG. 14c shows a downward/inward force arrow 54a indicating a direction in which the screen 404 is pushed or guided into the separation.

FIGS. 15a,b and 16a,b show a modified vertical riser 502 comprising bundled tubes 504 secured together at spaced intervals by connectors 506. The normal movement of the patient tends to alternately compress and expand the vertical risers 502, thus providing a "pumping" action for transferring fluid from the wound 4, as indicated by the fluid flow arrows 510. FIGS. 15a,b show a riser 502 in an extended configuration. Compressing the screen 14 longitudinally (i.e., end-to-end) compresses the bundled risers 504 to the configuration shown in FIGS. 16a,b, whereby fluid is drawn into the interstitial space 508 and pumped therefrom when the risers 502 extend.

FIG. 17 shows yet another configuration of a vertical riser 602 with bundled tubes 604, which are closely bunched and define passages 606 for conveying fluid. Such fluid conveyance can be enhanced by a pumping action associated with normal patient movements. Barbs 608 project outwardly from the tubes 604. It will be appreciated that various other bundled tube configurations, such as twisted, braided, etc., can be utilized.

Figure 18:
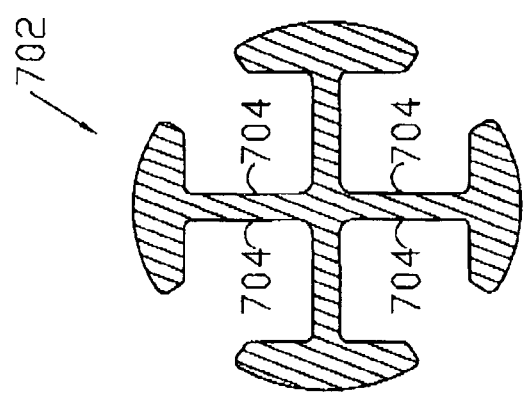
FIG. 18 is a cross-sectional view of a modified vertical riser or perimeter element, comprising a fluted tube.

FIG. 18 shows yet another vertical riser/perimeter member 702 alternative embodiment configuration. The member 702 has a configuration which is commonly referred to as a "fluted" drain and includes longitudinally-extending passages 704. This configuration can substitute for the perimeter members described above and can function to communicate fluid to and from the wound 4 with the input/output subsystem 18.

As additional alternative embodiment configurations for the vertical risers, they can comprise either barbed monofilament strands, similar to strand 30 shown in FIG. 3, or unbarbed monofilament strands. Such monofilament vertical risers can function as passive drains with fluid flowing alongside same. They can extend above the dermis 6 and abut or connect to transfer elements formed in various configurations with suitable absorbent materials. Examples include gauze dressings and transfer element subassemblies, such as 59 shown in FIG. 7d.

Figure 19:
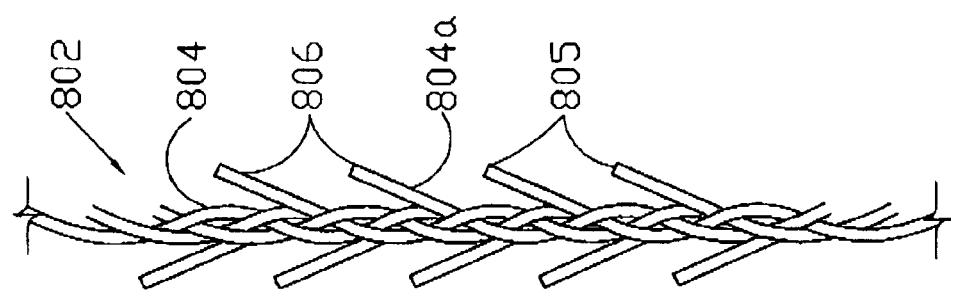
FIG. 19 is an enlarged, fragmentary, side elevational view of a modified barbed strand configuration.

FIG. 19 shows an alternative embodiment strand 802 constructed by twisting and braiding multiple, individual filaments 804. Barbs 805 are formed by respective individual filaments 804a, which terminate at blunt ends 806. The barbs 805 project generally outwardly from the strand 802 and form acute angles with respect to its longitudinal axis. They are adapted for penetrating tissue within a separation 4, as described above. In use, the barbs 805 would normally be oriented in directions generally pointing outwardly from the patient and the tissue separation 4.

Figure 20:
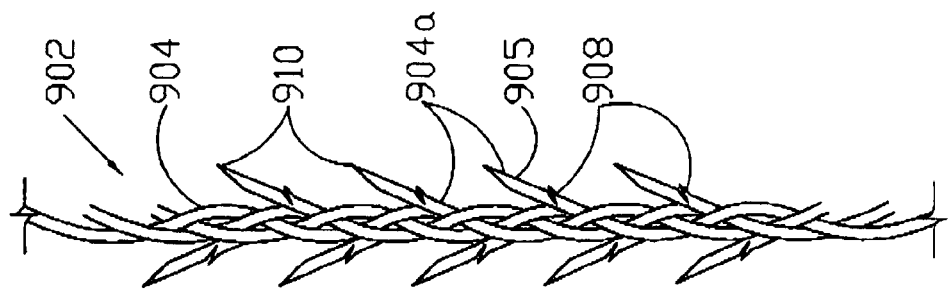
FIG. 20 is an enlarged, fragmentary, side elevational view of another modified barbed strand configuration.

FIG. 20 shows another alternative embodiment strand 902 comprising multiple twisted and braided filaments 904. Barbs 905 are formed from individual filaments 904a and have notches 908 and pointed ends 910. The notches 908 and the ends 910 are configured to allow the barbs 905 to easily extract from the separation edge tissues, whereby the screen is adapted for sliding along the separation edges in order to achieve the proper position.

FIG. 21 shows a further modified screen 1002 with barbs 1004 formed by looping individual filaments 1006 and cutting same at cut locations 1010 spaced inwardly from respective apexes 1008 of the filament loops. In operation, the barbs 1004 slightly penetrate the tissue and are imbedded therein. It will be appreciated that the filaments 1006 are relatively thin in diameter, similar to microfibers, whereby patient comfort is optimized.

FIG. 22 shows yet another modified screen 1102 with barbs 1104 formed by looping individual filaments 1106 and cutting same at locations 1110 spaced inwardly from respective apexes 1108 of the filament loops whereby respective hooks 1112 are formed. The hooks 1112 operate in a manner similar to hook-and-loop fasteners, with the adjacent tissue forming the loop parts of the connections. In operation, the hooks 1112 slightly penetrate the tissue and are imbedded therein. The configurations of the hooks 1112 tend to retain them in the tissue adjacent to the separation 4 whereby the separated first and second tissue portions 12*a,b* can be closed.

FIG. 23 shows a screen 1202 with a configuration similar to the screen. 1002 discussed above, with additional fiber elements or filaments 1204. The additional filaments 1204 tend to lay the filament barbs 1206 over whereby the screen 1202 can be directionally oriented within the wound separation 4 and operate in a manner similar to the screen 14 described above. The barbs 1206 are formed by cutting the apexes 1208 at cut locations 1210.

Similarly, FIG. 24 shows a screen 1302 with additional filaments 1304, which engage the filament loops 1306 and orient same in a direction towards the right as shown in FIG. 24. The slanted orientations of the filament loops 1306 facilitate setting same in the tissue portions 12*a,b* adjacent to the separation 4 by tugging outwardly on the screen 1302. Repositioning the screen 1302 is also possible, as described above. The filament loops 1306 can be cut at cut locations 1310, which are spaced inwardly from filament loop apexes 1308 whereby hooks 1312 are formed.

It will be appreciated that FIGS. 21-24 disclose screens with barbs and hooks extending from one face thereof. The present invention also includes screens with barbs and hooks extending from both faces.

It is to be understood that while certain forms of the present invention have been illustrated and described herein, it is not to be limited to the specific forms or arrangement of parts described and shown.

Having thus described the invention, what is claimed as new and desired to be secured by Letters Patent is:

1. A device for primary intention closing a separation of first and second portions of body tissue presenting first and second tissue generally matching edges respectively, which device comprises:
   a closure member with a perimeter and generally planar first and second faces, said perimeter having a first closure member edge;
   said closure member being adapted for positioning at least partly within said separation;
   first and second groups of multiple barbs associated with said first and second faces respectively and retaining same contact with said first and second body tissue portions respectively, said barbs including a directional tissue-sliding construction adapted for releasing one of said tissue edges and sliding one of said tissue edges relative to the other in a predetermined direction, said construction comprising an acute angular orientation of said barbs and adapted for closing said tissue portions in response to an outwardly directed force on said closure member such that all of said barbs extending from each said face are generally parallel with the other barbs extending from said face; and all of said barbs associated with both of said faces are generally oriented towards said first closure member edge;
   a pressure differential source associated with said closure member and adapted for exerting a pressure differential at said separation for approximating said tissue edges with said tissue edges maintained in repositionable alignment with respect to each other by said closure member; and
   a tube connected to said closure member and said pressure differential source, said tube including an orifice adapted for placement at said separation in direct fluidic connection with the tissue edges for applying the pressure differential directly thereto, said tube having an external port for fluid input/output.

2. The device according to claim 1 wherein said closure member comprises a screen with proximate and distal margins, multiple strands extending between said margins and each strand including multiple barbs projecting outwardly therefrom.

3. The device according to claim 1, which includes:
   said tube comprising a perimeter tube attached to said closure member perimeter and having first and second tube ends; and
   said pressure differential source being connected to said perimeter tube first end and adapted for exerting said pressure differential in said separation through said perimeter tube.

4. The device according to claim 1, which includes:
   said tube comprising a perimeter tube attached to said closure member perimeter and having first and second tube ends; and
   first and second input/output devices connected to said perimeter tube first and second ends respectively and adapted for fluidically communicating with said separation.

5. The device according to claim 1 wherein said closure member comprises a screen adapted to receive an ingrowth of tissue into said screen.

6. The device according to claim 1, which includes:
   said closure member having multiple risers adapted for extending within said separation.

7. The device according to claim 6 wherein each said riser has a monofilament construction and is adapted for communicating fluid therealong.

8. The device according to claim 6 wherein each said riser includes multiple barbs projecting outwardly in opposite directions from said first and second closure member faces.

9. The device according to claim 8 wherein each said barb includes a sharpened end and extends generally outwardly with respect to said separation.

10. The device according to claim 4 wherein one of said input/output devices comprises a fluid transfer subassembly.

11. The device according to claim 10 wherein said fluid transfer subassembly includes first and second sponges located on either side of said closure member on the skin surface and a bridge sponge placed over said first and second sponges.

12. The device according to claim 11 wherein said fluid transfer subassembly is connected to a vacuum source comprising said first input/output device.

13. The device according to claim 4 wherein said closure screen includes hollow risers, which fluidly communicate with said perimeter tube.

14. The device according to claim 13 wherein said risers include perforations.

15. The device according to claim 1, which includes a perimeter suture mounted on said closure member perimeter.

16. The device according to claim 15 wherein said perimeter suture includes first and second ends and first and second needles respectively mounted thereon.

17. The device according to claim 16 wherein said perimeter suture is separable from said closure member.

18. The device according to claim 2 wherein said strands comprise multi-filament, braided material.

19. The device according to claim 2 wherein said strands include filaments with free ends forming said barbs and projecting generally outwardly therefrom.

20. The device according to claim 19 wherein each barb includes a sharpened end and a notch spaced inwardly therefrom.

21. The device according to claim 6 wherein said risers comprise multiple members joined together and forming fluid passages therebetween.

22. The device according to claim 21 wherein said riser members are joined together at spaced intervals.

23. The device according to claim 22 wherein said risers are adapted for receiving fluid and pumping same in response to patient movements.

24. The device according to claim 21 wherein said risers comprise multiple, bundled tubes with multiple barbs projecting outwardly therefrom.

25. The device according to claim 4 wherein said perimeter tube comprises a fluted drain.

26. The device according to claim 1 wherein said closure member comprises a screen with a configuration adapted to admit tissue and body fluids.

27. The device according to claim 26 wherein said closure member screen consists of multiple strands forming a flexible panel.

28. The device according to claim 27 wherein each said strand has a respective barb.

29. The device according to claim 28, which includes said screen having multiple spacers connecting said strands and adapted for maintaining same in generally parallel, spaced relation.

30. The device according to claim 27 wherein:
said closure member screen has proximate and distal margins; and
each said strand includes multiple barbs extending therefrom in a direction generally outwardly and towards said distal margin.

31. The device according to claim 30 wherein said stands are integrally formed with said barbs.

32. The device according to claim 30 wherein:
each said strand comprises multiple filaments;
each said strand includes a longitudinally-extending axis; and
each said barb comprises a filament with a free end located in spaced relation from said axis.

33. The device according to claim 32 wherein said filaments are twisted.

34. The device according to claim 32 wherein said filaments are braided.

35. The device according to claim 26 wherein said closure screen comprises a biodegradable material adapted for absorption within said tissue separation.

36. The device according to claim 4 wherein one of said input/output devices is a fluid transfer element, which comprises a sponge material and is connected to said pressure differential source.

37. The device according to claim 36 wherein said fluid transfer element is connected to a fluid supply source, which irrigates said tissue separation.

38. The device according to claim 3 wherein one of said perimeter tube ends is closed.

39. The device according to claim 38, which includes a clamp mounted on said one perimeter tube end and adapted for closing same.

40. The device according to claim 38 wherein said one perimeter tube end is knotted.

41. The device according to claim 38 wherein said one perimeter tube end terminates below the patient's dermis.

42. The device according to claim 2 wherein said closure screen includes a plurality of tubular risers, each said riser having a fluid passage and a fluid inlet/outlet orifice communicating with said separation.

43. The device according to claim 42 wherein said tube and said risers are fluidically interconnected to form a fluid distribution manifold at said screen perimeter and extending across an interior of said screen.

44. The device according to claim 4, which includes a Leur lock mounted on a respective perimeter tube end and comprising a respective input device.

45. The device according to claim 4, wherein said perimeter tube is secured to said closure member by dissolvable connectors.

46. The device according to claim 1, which includes a fluid transfer element connected to said closure member and comprising a hydrophobic material.

47. The device according to claim 1, which includes a fluid transfer element connected to said closure member and comprising a hydrophilic material.

48. The device according to claim 4, which includes a needle mounted on said perimeter tube and adapted for passing same through tissue, and said perimeter tube including multiple orifices.

49. The device according to claim 1, which includes a fluid receptacle fluidically connected to said pressure differential source.

50. A device for closing a separation of first and second portions of body tissue, which device comprises:
a closure member with a perimeter and first and second faces;
said closure member being adapted for positioning at least partly within said separation;
first and second retainers associated with said first and second faces respectively and retaining same in contact with said first and second body tissue portions respectively;
a perimeter tube attached to said closure member perimeter and having first and second tube ends;
first and second input/output devices connected to said perimeter tube first and second ends respectively and adapted for fluidically communicating with said separation; and
said closure screen includes hollow risers, which fluidly communicate with said perimeter tube.

51. The device according to claim 50 wherein said risers include perforations.

52. A device for closing a separation of first and second portions of body tissue, which device comprises:
a closure member with a perimeter and generally planar first and second faces, said perimeter having a first edge;
said closure member being adapted for positioning at least partly within said separation;
first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;

a perimeter tube attached to said closure member perimeter and having first and second tube ends;

first and second input/output devices connected to said perimeter tube first and second ends respectively and adapted for fluidically communicating with said separation;

one of said input/output devices comprising a fluid transfer subassembly; and said fluid transfer subassembly including first and second sponges located on either side of said closure member on the skin surface and a bridge sponge placed over said first and second sponges.

53. A device for closing a separation of first and second portions of body tissue, which device comprises:

a closure member with a perimeter and generally planar first and second faces, said perimeter having a first edge;

said closure member being adapted for positioning at least partly within said separation;

first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;

a perimeter tube attached to said closure member perimeter and having first and second tube ends;

first and second input/output devices connected to said perimeter tube first and second ends respectively and adapted for fluidically communicating with said separation; and said closure screen including hollow risers, which fluidly communicate with said perimeter tube.

54. A device for closing a separation of first and second portions of body tissue, which device comprises:

a closure member with a perimeter and generally planar first and second faces, said perimeter having a first edge;

said closure member being adapted for positioning at least partly within said separation;

first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;

said closure member having multiple risers adapted for extending within said separation;

said risers comprising multiple riser members joined together and forming fluid passages;

said riser members being joined together at spaced intervals; and said risers being adapted for receiving fluid and pumping same in response to patient movements.

55. A device for closing a separation of first and second portions of body tissue, which device comprises:

a closure member with a perimeter and generally planar first and second faces, said perimeter having a first edge;

said closure member being adapted for positioning at least partly within said separation;

first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;

said closure member having multiple risers adapted for extending within said separation;

said risers comprise multiple members joined together and forming fluid passages; and said risers comprise multiple, bundled tubes with multiple barbs projecting outwardly therefrom.

56. A device for closing a separation of first and second portions of body tissue, which device comprises:

a closure member with a perimeter and generally planar first and second faces, said perimeter having a first edge;

said closure member being adapted for positioning at least partly within said separation; and first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;

a perimeter member attached to said closure member perimeter and having first and second ends;

said perimeter member comprising a tube adapted for fluidically communicating with said tissue within said tissue separation;

a pressure gradient source connected to said perimeter tube first end;

first and second input/output devices connected to said perimeter tube first and second ends respectively and adapted for fluidically communicating with said separation;

one of said input/output devices is a fluid transfer element, which comprises a sponge material and is connected to said pressure gradient source; and said fluid transfer element is connected to a fluid supply source, which irrigates said tissue separation.

57. A device for closing a separation of first and second portions of body tissue, which device comprises:
a closure member with a perimeter and generally planar first and second faces, said perimeter having a first edge;
said closure member being adapted for positioning at least partly within said separation;
first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;
a perimeter member attached to said closure member perimeter and having first and second ends;
said perimeter member comprising a tube adapted for fluidically communicating with said tissue within said tissue separation;
one of said perimeter tube ends being closed; and
said one perimeter tube end being knotted.

58. A device for closing a separation of first and second portions of body tissue, which device comprises:
a closure member with a perimeter and generally planar first and second faces, said perimeter having a first edge;
said closure member being adapted for positioning at least partly within said separation;
first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;
a perimeter member attached to said closure member perimeter and having first and second ends;
said perimeter member comprising a tube adapted for fluidically communicating with said tissue within said tissue separation; and
said closure screen including a plurality of tubular risers, each said riser having a fluid passage and a fluid inlet/outlet orifice communicating with said separation.

59. A device for closing a separation of first and second portions of body tissue, which device comprises:
a closure member with a perimeter and generally planar first and second faces, said perimeter having a first edge;
said closure member being adapted for positioning at least partly within said separation;
first and second groups of multiple retainers comprising barbs associated with said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said Face are generally parallel with the other barbs extending from said face; and all of said barbs are generally oriented towards said first edge;
a perimeter member attached to said closure member perimeter and having first and second ends;
said perimeter member comprising a tube adapted for fluidically communicating with said tissue within said tissue separation;
a needle mounted on said perimeter tube and adapted for passing same through tissue; and
said perimeter tube including multiple orifices.

60. A device for closing a separation of first and second portions of body tissue, which device comprises:
a closure member with a perimeter and generally planar first and second faces, said closure member being adapted for placement at least partly in said separation and said perimeter having a first edge;
a tube connected to said closure member and including an orifice adapted for placement at said separation in fluidic connection with the patient, said tube having an external port for fluid input/output;
first and second groups of multiple barbs associated with and extending from said first and second faces respectively and retaining same in contact with said first and second body tissue portions respectively, said barbs including a directional tissue-sliding construction adapted for sliding one of said tissue portions relative to the other in a predetermined direction, said construction comprising an acute angular orientation of said barbs and adapted for closing said tissue portions in response to an outwardly directed force on said closure member such that all of said barbs extending from said face are generally parallel with the other barbs extending from said face; and all of said barbs are generally oriented towards said first edge;
said tube comprising a perimeter tube mounted on said closure member perimeter and including multiple input/output orifices;
an external suction/supply source;
said closure member including a plurality of risers each having multiple inlet/outlet orifices and connected to an external suction/supply source; and
said perimeter tube external port being connected to said external suction/supply source.

61. A device for closing a separation of first and second portions of body tissue, which device comprises:
a closure member with a perimeter and first and second faces;
said closure member being adapted for positioning at least partly within said separation;
first arid second retainers associated with said first and second faces respectively and retaining same in contact with said first and second body tissue portions respectively;
a perimeter tube attached to said closure member perimeter and having first and second tube ends;

first and second input/output devices connected to said perimeter tube first and second ends respectively and adapted for fluidically communicating with said separation;

one of said input/output devices comprising a fluid transfer subassembly; and said fluid transfer subassembly including first and second sponges located on either side of said closure member on the skin surface and a bridge sponge placed over said first and second sponges.

62. A device for closing a separation of first and second portions of body tissue, which device comprises:

a closure member with a perimeter and first and second faces;

said closure member being adapted for positioning at least partly within said separation;

first and second retainers associated with said first and second faces respectively and retaining same in contact with said first and second body tissue portions respectively;

said closure member having multiple risers adapted for extending within said separation;

said risers comprising multiple members joined together and forming fluid passages therebetween;

said risers being joined together at spaced intervals; and said risers being adapted for receiving fluid and pumping same in response to patient movements.

63. A device for closing a separation of first and second portions of body tissue, which device comprises:

a closure member with a perimeter and first and second faces;

said closure member being adapted for positioning at least partly within said separation;

first and second retainers associated with said first and second faces respectively and retaining same in contact with said first and second body tissue portions respectively;

said closure member having multiple risers adapted for extending within said separation;

said risers comprising multiple members joined together and forming fluid passages therebetween; and said risers comprising multiple, bundled tubes with multiple barbs projecting outwardly therefrom.

64. A device for closing a separation of first and second portions of body tissue, which device comprises:

a closure member with a perimeter and first and second faces;

said closure member including a barb projecting outwardly from said first closure member face;

said barb being adapted to penetrate the first portion of said tissue with said closure member positioned at least partly in said separation and with said separated tissue portions engaging said closure member;

a perimeter member attached to said closure member perimeter and having first and second ends;

said perimeter member comprising a tube adapted for fluidically communicating with said tissue within said tissue separation;

a pressure gradient source connected to said perimeter tube first end;

first and second input/output devices connected to said perimeter tube first and second ends respectively and adapted for fluidically communicating with said separation;

one of said input/output devices comprising a fluid transfer element, which comprises a sponge material and is connected to said pressure gradient source; and said fluid transfer element is connected to a fluid supply source, which irrigates said tissue separation.

65. A device for closing a separation of first and second portions of body tissue, which device comprises:

a closure member with a perimeter and first and second faces;

said closure member including a barb projecting outwardly from said first closure member face;

said barb being adapted to penetrate the first portion of said tissue with said closure member positioned at least partly in said separation and with said separated tissue portions engaging said closure member;

a perimeter member attached to said closure member perimeter and having first and second ends;

said perimeter member comprising a tube adapted for fluidically communicating with said tissue within said tissue separation;

one of said perimeter tube ends being closed; and said one perimeter tube end being knotted.

66. A device for closing a separation of first and second portions of body tissue, which device comprises:

a closure member with a perimeter and first and second faces;

said closure member including a barb projecting outwardly from said first closure member face;

said barb being adapted to penetrate the first portion of said tissue with said closure member positioned at least partly in said separation and with said separated tissue portions engaging said closure member;

a perimeter member attached to said closure member perimeter and having first and second ends;

said perimeter member comprising a tube adapted for fluidically communicating with said tissue within said tissue separation; and said closure screen including a plurality of tubular risers, each said riser having a fluid passage and a fluid inlet/outlet orifice communicating with said separation.

* * * * *